US007485432B2

(12) United States Patent
Fink et al.

(10) Patent No.: US 7,485,432 B2
(45) Date of Patent: Feb. 3, 2009

(54) SELECTIVE MODULATION OF TLR-MEDIATED BIOLOGICAL ACTIVITY

(75) Inventors: Jason R. Fink, Eagan, MN (US); Keith B. Gorden, Maplewood, MN (US); Kevin S. Gorski, White Bear Lake, MN (US); Shalley K. Gupta, Woodbury, MN (US); Xiaohong Qiu, Rosemount, MN (US); John P. Vasilakos, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 324 days.

(21) Appl. No.: 10/788,731

(22) Filed: Feb. 27, 2004

(65) Prior Publication Data

US 2004/0171086 A1  Sep. 2, 2004

Related U.S. Application Data

(60) Provisional application No. 60/450,484, filed on Feb. 27, 2003.

(51) Int. Cl.
*G01N 33/53* (2006.01)
*G01N 33/567* (2006.01)
*C12N 15/06* (2006.01)
*C12P 21/02* (2006.01)
*C07K 14/435* (2006.01)

(52) U.S. Cl. .................. 435/7.21; 435/7.2; 435/252.3; 435/471; 435/69.1; 530/350; 536/23.5

(58) Field of Classification Search .................. None
See application file for complete search history.

(56) References Cited

U.S. PATENT DOCUMENTS

| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster et al. |
| 5,268,376 A | 12/1993 | Gerster |
| 5,346,905 A | 9/1994 | Gerster |
| 5,352,784 A | 10/1994 | Nikolaides et al. |
| 5,367,076 A | 11/1994 | Gerster |
| 5,376,501 A | 12/1994 | Mariën et al. |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,605,899 A | 2/1997 | Gerster et al. |
| 5,693,811 A | 12/1997 | Lindstrom |
| 5,741,908 A | 4/1998 | Gerster et al. |
| 5,756,747 A | 5/1998 | Gerster |
| 5,939,090 A | 8/1999 | Beaurline et al. |
| 6,028,076 A | 2/2000 | Hirota et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,113,918 A | 9/2000 | Johnson et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,303,347 B1 | 10/2001 | Johnson et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,376,501 B1 | 4/2002 | Isobe et al. |
| 6,376,669 B1 | 4/2002 | Rice et al. |
| 6,387,938 B1 | 5/2002 | Mizuguchi et al. |
| 6,406,705 B1 | 6/2002 | Davis et al. |

(Continued)

FOREIGN PATENT DOCUMENTS

| EP | 0 394 026 | 10/1990 |
| EP | 1 104 764 A1 | 6/2001 |
| JP | 9-208584 | 8/1997 |
| JP | 11-80156 | 3/1999 |
| JP | 11-222432 | 8/1999 |

(Continued)

OTHER PUBLICATIONS

Gibson et al, cellular Immunology, Aug. 2002, vol. 218, pp. 74-86.*
Testerman, et al., "Cytokine Induction by the Immunomodulators Imiquimod and S-27609", *Journal of Leukocyte Biology*, vol. 58, pp. 365-372, Sep. 1995.
Chollet, et al, "Development of a Topically Active Imiquimod Formulation", *Pharmaceutical Development and Technology*, 4(1), pp. 35-43 (1999).

(Continued)

*Primary Examiner*—Bridget E Bunner
*Assistant Examiner*—Fozia M Hamud

(57) ABSTRACT

Methods of identifying a compound that selectively modulates at least one TLR-mediated cellular activity are disclosed. Generally, the methods include identifying a compound as a compound that selectively modulates at least one TLR-mediated cellular activity if the compound modulates one TLR-mediated cellular activity to a different extent than it modulates a second TLR-mediated cellular activity. Compounds so identified and pharmaceutical compositions including such compounds are also disclosed. Methods of selectively modulating immune cells and methods of treating certain conditions are also provided. Such methods include administering to cells or a subject a compound that selectively modulates a TLR-mediated cellular activity.

9 Claims, 2 Drawing Sheets

U.S. PATENT DOCUMENTS

| | | |
|---|---|---|
| 6,426,334 B1 | 7/2002 | Agrawal et al. |
| 6,440,992 B1 | 8/2002 | Gerster et al. |
| 6,451,810 B1 | 9/2002 | Coleman et al. |
| 6,476,000 B1 | 11/2002 | Agrawal |
| 6,514,985 B1 | 2/2003 | Gerster et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0110840 A1 | 8/2002 | Tomai et al. |
| 2003/0022302 A1 | 1/2003 | Lewis et al. |
| 2003/0104523 A1 | 6/2003 | Bauer et al. |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0199461 A1 | 10/2003 | Averett et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |

FOREIGN PATENT DOCUMENTS

| | | |
|---|---|---|
| JP | 2000-247884 | 9/2000 |
| WO | WO 00/47719 A2 | 8/2000 |
| WO | WO 00/75304 A1 | 12/2000 |
| WO | WO 00/76505 A1 | 12/2000 |
| WO | WO 00/76518 A1 | 12/2000 |
| WO | WO 01/74343 A2 | 10/2001 |
| WO | WO 02/36592 A1 | 5/2002 |
| WO | WO 02/46188 A2 | 6/2002 |
| WO | WO 02/46189 A2 | 6/2002 |
| WO | WO 02/46190 A2 | 6/2002 |
| WO | WO 02/46191 A2 | 6/2002 |
| WO | WO 02/46192 A2 | 6/2002 |
| WO | WO 02/46193 A2 | 6/2002 |
| WO | WO 02/46194 A2 | 6/2002 |
| WO | WO 02/46749 A2 | 6/2002 |
| WO | WO 02/085905 A1 | 10/2002 |
| WO | WO 02/102377 A1 | 12/2002 |
| WO | WO 03/020889 A2 | 3/2003 |
| WO | WO 03/043572 A2 | 5/2003 |
| WO | WO 03/045391 A1 | 6/2003 |
| WO | WO 03/089602 | 10/2003 |
| WO | WO 03/103584 A2 | 12/2003 |

OTHER PUBLICATIONS

Brassard et al.; "Interferon-α as an immunotherapeutic protein"; Journal of Leukocyte Biology; vol. 71; Apr. 2002; pp. 565-581.

Izumi et al.; "1H-imidazo[4,5-c]quinoline Derivatives as Novel Potent TNF-α Suppressors: Synthesis and Structure-Activity Relationship of 1-, 2-and 4-Substituted 1H-imidazo[4,5-c]quinolines or 1H-imidazo[4,5-c]pyridines"; *Bioorganic and Medicinal Chemistry*, vol. 11, pp. 2541-2550 (2003).

Hornung et al., "Quantitative Expression of Toll-Like Receptor 1-10 mRNA in Cellular Subsets of Human Peripheral Blood Mononuclear Cells and Sensitivity to CpG Oligodeoxynucleotides[1]", *The Journal of Immunology*, 2002, 168; pp. 4531-4537.

Hemmi et al., "Small anti-viral compounds activate immune cells via the TLR7 MyD88-dependent Signaling pathway", *Nature Immunology*, vol. 3, No. 2; Feb. 2002; pp. 196-200.

Medzhitov, "Toll-Like Receptors and Innate Immunity", *Nature Reviews Immunology*, vol. 1; Nov. 2001, pp. 135-145.

Jurk et al. "Human TLR7 and TLR8 independently confer responsiveness to the antiviral compound R-848", *Nature Immunology*, Jun. 2002, vol. 3, No. 6; p. 1.

Akira et al., "Toll-like receptors: critical proteins linking innate and acquired immunity", *Nature Immunology*, Aug. 2001, vol. 2, No. 8; pp. 675-680.

Heil et al.; "Synthetic Immunostimulatory compounds activate immune cells via TLR7 and TLR8"; 33th Annual Meeting of the Deutsche Gessellschaft für Immunologie, Marburg 2002—Abstract C.6.

Akira S. et al., Recognition of pathogen-associated molecular patterns by TLR family. Immuno. Letters. 2003, vol. 85, pp. 85-95.

Ozinsky A. et al., The repertoire for pattern recognition of pathogens by the innate immune system is defined by cooperation between Toll-like receptors, PNAS, Dec. 5, 2000, vol. 97, No. 25, pp. 13766-13771.

Gorden et al., "Synthetic TLR Agonists Reveal Functional Differences between Human TLR7 and TLR8", *The Journal of Immunology*, 2005, vol. 174, pp. 1259-1268.

Sauder et al., "Randomized, Single-Blind, Placebo-Controlled Study of Topical Application of the Immune Response Modulator Resiquimod in Healthy Adults", *Antimicrobial Agents and Chemotherapy*, Dec. 2003, vol. 47, No. 12, pp. 3846-3852.

* cited by examiner

SELECTIVE MODULATION OF TLR-MEDIATED BIOLOGICAL ACTIVITY

CROSS-REFERENCE TO RELATED APPLICATION

This application claims priority to U.S. Provisional Patent Application No. 60/450,484, filed Feb. 27, 2003.

BACKGROUND

Immune response modifiers ("IRMs") include compounds that possess potent immunomodulating activity including but not limited to antiviral and antitumor activity. Certain IRMs activate the production and secretion of cytokines. For example, certain IRM compounds induce the production and secretion of cytokines such as, e.g., Type I interferons, TNF-α IL-1, IL-6, IL-8, IL-10, IL-12, MIP-1, and/or MCP-1. As another example, certain IRM compounds can inhibit production and secretion of certain $T_H2$ cytokines, such as IL-4 and IL-5. Additionally, some IRM compounds are said to suppress IL-1 and TNF (U.S. Pat. No. 6,518,265).

Certain IRMs are small organic molecules (e.g., molecular weight under about 1000 Daltons, preferably under about 500 Daltons, as opposed to large biological molecules such as proteins, peptides, and the like) such as those disclosed in, for example, U.S. Pat. Nos. 4,689,338; 4,929,624; 4,988,815; 5,037,986; 5,175,296; 5,238,944; 5,266,575; 5,268,376; 5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,539; 6,376,669; 6,451,810; 6,525,064; 6,541,485; 6,545,016; 6,545,017; 6,558,951; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; European Patent 0 394 026; U.S. Patent Publication Nos. 2002/0016332; 2002/0055517; 2002/0110840; 2003/0133913; 2003/0199538; and 2004/0014779; and International Patent Publication Nos. WO 01/74343; WO 02/46749 WO 02/102377; WO 03/020889; WO 03/043572; WO 03/045391; and WO 03/103584.

Additional examples of small molecule IRMs include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/085905), and certain 3-β-D-ribofuranosylthiazolo[4,5-d]pyrimidine derivatives (such as those described in U.S. Publication No. 2003/0199461).

Other IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunoactivatory structural motifs such as those described, for example, in U.S. Pat. Nos. 6,426,334 and 6,476,000. Other IRM nucleotide sequences lack CpG and are described, for example, in International Patent Publication No. WO 00/75304.

By stimulating certain aspects of the immune system, as well as suppressing other aspects (see, e.g., U.S. Pat. Nos. 6,039,969 and 6,200,592), IRMs may be used to treat many diseases. For example, diseases that may be treated using IRM compounds include, but are not limited to, external genital and perianal warts caused by human papillomavirus, basal cell carcinoma, eczema, essential thrombocythaemia, hepatitis B, multiple sclerosis, neoplastic diseases, psoriasis, rheumatoid arthritis, type I herpes simplex, and type II herpes simplex.

IRM compounds can modulate cell-mediated immunity by inducing secretion of certain immune system regulator molecules such as cytokines. For example, cytokines that are induced by imiquimod or resiquimod include but are not limited to Type I interferons, TNF-α, IL-1, IL-6, IL-8, IL-10, IL-12, MIP-1, and MCP-1.

IRM compounds also can modulate humoral immunity by stimulating antibody production by B cells. Further, various IRMs have been shown to be useful as vaccine adjuvants (see, e.g., U.S. Pat. Nos. 6,083,505 and 6,406,705).

SUMMARY

The present invention provides a method of identifying a compound that selectively modulates at least one TLR-mediated cellular activity. Generally, the method includes providing an assay to detect modulation of a TLR-mediated cellular activity for each of a plurality of TLRs; performing each assay using a test compound; and identifying the test compound as a compound that selectively modulates at least one TLR-mediated cellular activity if the test compound modulates a first TLR-mediated cellular activity to a different extent than it modulates at least one second TLR-mediated cellular activity.

The present invention also provides compounds thus identified, as well as pharmaceutical compositions that include such a compound or a prodrug of such a compound.

In another aspect, the present invention provides a method of identifying a target compound having a target TLR modulation profile. Generally, the method includes selecting a target TLR modulation profile; determining the TLR modulation profile of a test compound; and identifying the test compound as a target compound if the TLR modulation profile of the test compound conforms to the target TLR modulation profile.

The present invention also provides compounds thus identified, as well as pharmaceutical compositions that include such a compound or a prodrug of such a compound.

In another aspect, the present invention provides a method of selectively modulating cells of the immune system. Generally, the method includes identifying a first immune system cell population and a second immune system cell population; selecting a compound that modulates a TLR-mediated cellular activity of the first cell population to a different extent than it modulates a TLR-mediated cellular activity of the second cell population; and contacting cells of the immune system with the selected compound in an amount effective to modulate a TLR-mediated cellular activity of at least one of the cell populations.

In some embodiments, modulating a TLR-mediated cellular activity of the cells of the immune system can include activating the TLR-mediated cellular activity of the cells or inhibiting the TLR-mediated cellular activity of the cells. Additionally, the TLR-mediated cellular activity of the cells may be modulated in vitro or in vivo.

In another aspect, the present invention provides a method of treating a condition treatable by selectively modulating at least one TLR-mediated cellular activity in a subject. Generally, the method includes identifying a target TLR modulation profile effective for treating the condition; selecting an IRM compound having a TLR modulation profile that conforms to the target profile; and administering to the subject an amount of the IRM compound effective for treating the condition.

Conditions that may be treated according to methods of the present invention include but are not limited to neoplastic diseases, $T_H1$-mediated diseases, $T_H2$-mediated diseases, and infectious diseases (e.g., viral diseases, bacterial diseases, fungal diseases, parasitic diseases, protozoal diseases, prion-mediated diseases, and the like).

Various other features and advantages of the present invention should become readily apparent with reference to the following detailed description, examples, claims, and appended figures. In several places throughout the specification, guidance is provided through lists of examples. In each instance, the recited list serves only as a representative group and should not be interpreted as an exclusive list.

DETAILED DESCRIPTION OF ILLUSTRATIVE EMBODIMENTS OF THE INVENTION

Figure 1:
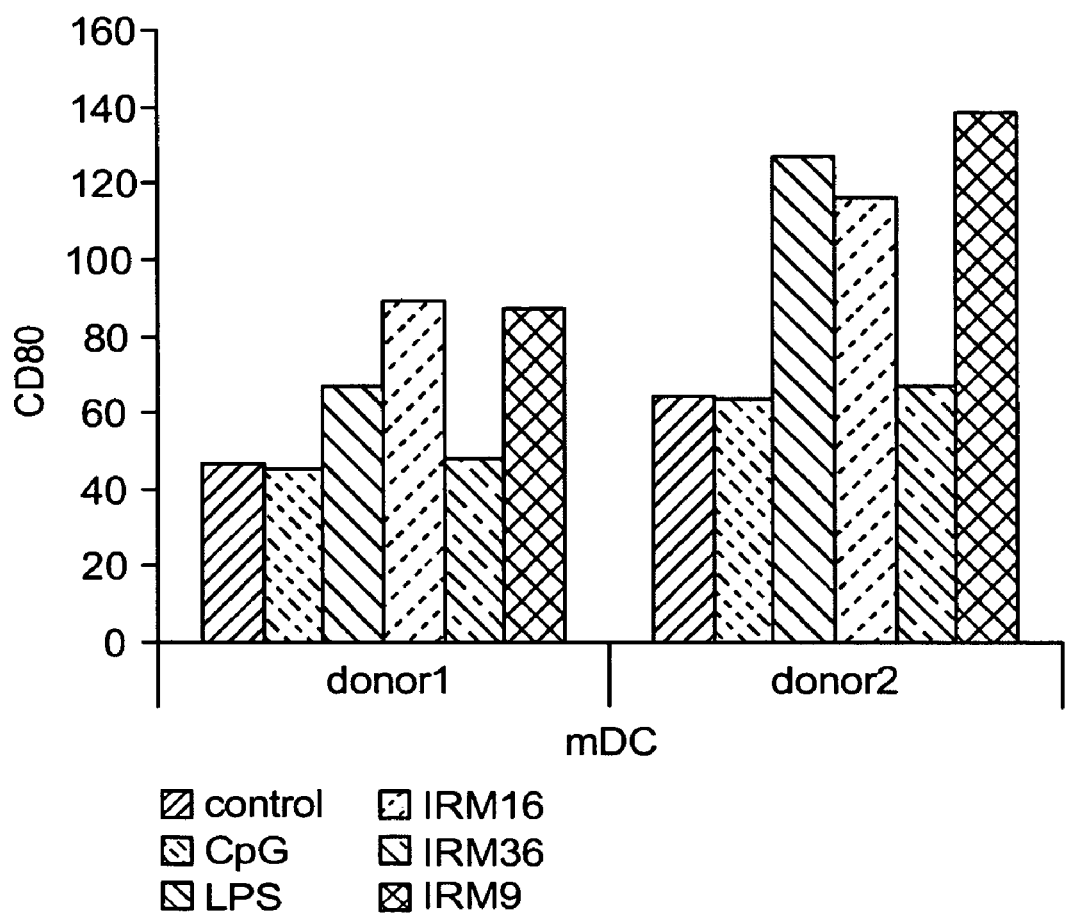
FIG. 1 is a bar graph showing selective activation of myeloid dendritic cells.

Certain IRMs can function as Toll-like receptor (TLR) agonists. It has been discovered that certain IRMs can selectively modulate one or more TLR-mediated cellular activities. In some cases, the selective modulation involves modulating one TLR-mediated cellular activity, but not detectably modulating another TLR-mediated cellular activity. In other cases, selective modulation involves modulating one TLR-mediated cellular activity to an extent that differs from the extent to which another TLR-mediated cellular activity is modulated.

Accordingly, the present invention provides methods of identifying compounds that selectively modulate a TLR-mediated cellular activity, the compounds thus identified, and pharmaceutical compositions including such compounds; methods of identifying compounds having a particular TLR modulation profile, the compounds thus identified, and pharmaceutical compositions including such compounds; methods of selectively modulating certain populations of immune cells; and methods of treating a subject by administering to the subject a compound that selectively modulates at least one TLR-mediated cellular activity.

For purposes of this invention, the following terms shall have the following meanings.

"Activate" and variations thereof refer to any measurable increase in cellular activity.

"Agonist" refers to a compound that can combine with a receptor (e.g., a TLR) to produce a cellular activity. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the receptor. An agonist may be referred to as an agonist of a particular TLR (e.g., a TLR6 agonist) or a particular combination of TLRs (e.g., a TLR 7/8 agonist—an agonist of both TLR7 and TLR8).

"Cellular activity" refers to a biological activity (e.g., cytokine production) that results from an agonist-receptor interaction.

"Inhibit" and variations thereof refer to any measurable reduction of cellular activity. Thus, as used herein, "inhibit" or "inhibition" may be referred to as a percentage of a normal level of activity.

"IRM compound" refers to a compound that alters the level of one or more immune regulatory molecules (e.g., cytokines, co-stimulatory markers, or maturation markers) when administered to an IRM-responsive cell. Representative IRM compounds include the small organic molecules, purine derivatives, small heterocyclic compounds, amide derivatives, and oligonucleotide sequences described above.

"Modulate" and variations thereof refer to a substantial increase or decrease in biological activity. A substantial increase or decrease in biological activity is an increase or decrease beyond a desired threshold increase or decrease in the biological activity.

"Prodrug" refers to a derivative of a drug molecule that requires a chemical or enzymatic biotransformation in order to release the active parent drug in the body.

"Selective" and variations thereof refer to having a differential or a non-general impact on biological activity. An agonist that selectively modulates biological activity through a particular TLR may be a TLR-selective agonist. TLR-selectivity may be described with respect to a particular TLR (e.g., TLR8-selective) or with respect to a particular combination of TLRs (e.g., TLR 7/9-selective).

"TLR-mediated" refers to a biological or biochemical activity that results, directly or indirectly, from TLR function. A particular biological or biochemical activity may be referred to as mediated by a particular TLR (e.g., "TLR6-mediated" or "TLR7-mediated").

"TLR modulation profile" refers to a profile of one or more TLR-mediated cellular activities that can be modulated using an IRM compound. A target TLR modulation profile refers to a particular desired profile, i.e., a theoretical or idealized TLR modulation profile, such as for a target compound to be identified in a screening assay, or for a compound that would modulate biological activity of immune cells in a particular manner. The TLR modulation profile of a given compound refers to the observed profile of TLR-mediated cellular activities modulated by the given compound. The observed profile may be compiled from a single source or multiple sources and may be derived from, for example, experimental assay results, clinical or anecdotal observations, or any other suitable source.

In one aspect, the present invention provides a method of identifying a compound that selectively modulates at least one TLR-mediated cellular activity. In general, the method includes providing an assay to detect modulation of at least one TLR-mediated cellular activity for each of a plurality of TLRs; performing each assay using a test compound; and identifying the test compound as a compound that selectively modulates at least one TLR-mediated cellular activity if the test compound modulates a first TLR-mediated cellular activity to a different extent than it modulates at least one second TLR-mediated cellular activity.

The method may detect modulation of at least one TLR-mediated cellular activity by detecting an increase in a TLR-mediated cellular activity, a decrease in a TLR-mediated cellular activity, or both. For example, in some embodiments, the assays selected for practicing the method can include an assay that detects an increase in, for example, a TLR7-mediated cellular activity, and a second assay that detects an increase in, for example, a TLR8-mediated cellular activity. Such a method could identify compounds that either: (a) increase the TLR7-mediated cellular activity but do not modulate the TLR8-mediated cellular activity, (b) increase the TLR8-mediated cellular activity but do not modulate the TLR7-mediated cellular activity, or (c) increase both the TLR7-mediated cellular activity and the TLR8-mediated cellular activity, but do so to varying degrees. Additionally or alternatively, the method might include one or more assays that detect inhibition of a TLR-mediated cellular activity.

A compound that modulates a cellular activity mediated through one TLR or a particular combination of TLRs, but does not modulate cellular activity through other TLRs may be referred to as TLR-selective. For example, the term "TLR8-selective" may refer to a compound that modulates a TLR8-mediated cellular activity, but does not modulate cellular activity mediated through another TLR. Likewise, the term "TLR7-selective" may refer to a compound that modulates a TLR7-mediated cellular activity, but does not modulate cellular activity mediated by another TLR.

In some embodiments, a TLR-selective compound may mediate cellular activity through one or more TLRs. In such cases, "TLR selective" may refer to selectivity between two or more TLRs of particular interest such as, for example, TLR7 and TLR8. Accordingly, "TLR8-selective" may refer, in some embodiments, to a compound that modulates TLR8-mediated cellular activity, but does not modulate (i.e., does not substantially increase or decrease) cellular activity mediated through any other TLR (i.e., TLR8 only). In other embodiments, however, "TLR8-selective" may refer to a compound that modulates TLR8-mediated cellular activity and cellular activity modulated through one or more other TLRs, but does not modulate cellular activity mediated through one or more particular TLRs, for example, TLR7 (i.e., TLR8, but not TLR7).

Similarly, "TLR7-selective" may refer to a compound that modulates TLR7-mediated cellular activity, but does not modulate cellular activity through any other TLR (TLR7 only). Alternatively, "TLR7-selective" may refer to a compound that modulates TLR7-mediated cellular activity and cellular activity mediated by at least one other TLR, but does not modulate cellular activity mediated through one or more particular TLR, for example, TLR8 (TLR7, but not TLR8).

As noted above, TLR-selective compound may mediate cellular activity through a particular combination of TLRs, but does not modulate activity through another TLR. For example, a compound may mediate cellular activity through both TLR7 and TLR9, but not mediate cellular activity through TLR8. Depending upon the specific nature of the desired selectivity, such as compound may be referred to as, for example, TLR7-selective (if, e.g., TLR9-mediated cellular activity is not relevant), TLR9-selective (if, e.g., TLR7-mediated cellular activity is not relevant), or TLR7/9-selective (if, e.g., both TLR7-mediated cellular activity and TLR9-mediated cellular activity are relevant).

Certain compounds that may be useful for practicing certain methods of the invention, or that may be identified by practicing certain methods of the invention, may be considered to be TLR6-selective compounds. Other compounds may be considered to be TLR7-selective compounds. Still other compounds may be considered to be TLR8-selective compounds. Still other compounds may be considered to be TLR9-selective compounds.

Standard techniques are available that permit one to design and perform assays that can detect an increase or a decrease in a cellular activity mediated by any TLR. Suitable techniques are described, for example, in U.S. Patent Publication Nos. US 2004/0014779 A1, US 2004/0132079, US 2004/0197865, and US 2004/0162309.

Unless otherwise indicated, an increase or a decrease in cellular activity refers to an increase or decrease in a particular cellular activity compared to that observed in an appropriate control. An assay may or may not be performed in conjunction with the appropriate control. With experience, one skilled in the art may develop sufficient familiarity with a particular assay (e.g., the range of values observed in an appropriate control under specific assay conditions) that performing a control may not always be necessary to determine whether a compound modulates the TLR-mediated cellular activity in a particular assay.

The precise extent to which a TLR-mediated cellular activity is increased or decreased before it is considered substantial and, therefore, modulated for purposes of the invention may vary according to factors known in the art. Such factors may include, for example, the cellular activity observed as the endpoint of the assay, the concentration of the TLR agonist, the method used to measure or detect the endpoint of the assay, the signal-to-noise ratio of the assay, the precision of the assay, and the nature of different assays used to detect modulation of cellular activities mediated by different TLRs. Accordingly it is not practical to set forth generally the threshold increase of TLR-mediated cellular activity required to identify a compound as modulating a particular TLR-mediated cellular activity for all possible assays. Those of ordinary skill in the art, however, can readily determine the appropriate threshold with due consideration of such factors.

In some embodiments, for example, the threshold at which the change in cellular activity is considered "substantial" and, therefore, modulated may be at least a two-fold when a TLR agonist is provided at a given concentration. In other embodiments, the threshold at which the change in cellular activity is considered substantial and, therefore, modulated may be at least three-fold. I still other embodiments, the threshold change may be at least five-fold. An increase or decrease in a TLR-mediated cellular activity that fails to meet the threshold change may be considered to be insubstantial (i.e., not substantially changed) and, therefore, not modulated for purposes of the invention. Thus, a compound may be considered selective between two TLRs if, for example, the compound increases cellular activity mediated by each TLR, but increases the cellular activity mediated through one TLR to an extent greater than the threshold (i.e., modulated), but increases the cellular activity modulated through the other TLR to an extent less than the threshold necessary to be considered substantial (i.e., not modulated).

Cells used in the assays of the methods of the present invention may be any cells that express one or more TLRs and permit detection of TLR-mediated cellular activity. In some cases, the cells may naturally express one or more TLRs. Cells that naturally express one or more TLRs include, but are not limited to, primary immune cells such as monocytes, macrophages, Langerhans cells, dendritic cells, Natural Killer cells, polymorphonuclear cells (e.g., neutrophils, basophils, or eosinophils), B lymphocytes, T lymphocytes, and cells derived from any of the foregoing. In some embodiments, the cells may be genetically modified to increase their expression of one or more TLRs. Some genetically modified cells may be derived from host cells that naturally express one or more TLRs, but have been modified to increase expression of one or more TLRs or increase the number of TLRs expressed by the genetically modified cell. Other genetically modified cells may be derived from host cells that lack detectable TLR activity, so that any detectable TLR-mediated biological activity can be attributed to the one or more TLRs introduced into the cell by the genetic modification.

Some assays suitable for detecting TLR-mediated cellular activity include, but are not limited to, detecting expression and/or production of one or more cytokines, chemokines, co-stimulatory markers, or proliferation/maturation markers. Such cellular activity may be detected, for example, by detecting an increase in the presence of one or more such molecules in cell culture, either in the culture medium or sequestered within cells of the culture. In some embodiments, the TLR-mediated cellular activity may include production of at least one cytokine including such as, for example, TNF-α, a Type I interferon (e.g., IFN-α, IFN-β, IFN-ω, etc.), IFN-γ, IL-1, IL-6, IL-8, IL-10, IL-12, MIP-1, MCP-1, or any combination thereof. In other embodiments, the TLR-mediated cellular activity may include production of one or more co-stimulatory markers (e.g., CD40, CD80, CD86 etc.), an intercellular adhesion molecule (ICAM, e.g., ICAM-1, ICAM-2, I-CAM-3, etc.), or a proliferation/maturation marker such as, for example, CD83 or CCR7.

Alternatively, TLR-mediated activity may be detected by detecting induction of gene transcription from a promoter that controls expression of one or more cytokines, chemokines, co-stimulatory markers, or maturation markers. For example, an assay may be designed to detect TLR-mediated activation of a promoter such as the NFκB promoter or the IFN-α1 promoter. As noted above, in some embodiments, detecting TLR-mediated activation of these promoters may include detection of the molecule produced from the induced gene. Alternatively, some assays may be designed so that a reporter gene is operably linked to a TLR-induced promoter—e.g., the NFκB promoter or the IFN-α1 promoter—so that TLR-mediated induction of the promoter may be readily detected. Many gene expression reporter constructs are commercially available. In one embodiment, a luciferase reporter system may be operably linked to a TLR-inducible promoter such as the NFκB promoter or the IFN-α1 promoter, so that TLR-mediated induction of the promoter may be detected by detecting the resulting luciferase signal.

In one embodiment, exemplified in Example 1, selective modulation between TLR7 and TLR8 was observed in genetically modified HEK293 cells by detecting TLR-mediated NFκB-induced transcription of a luciferase reporter. Results are shown in Table 5 and are expressed as the fold increase in NFκB-induced luciferase signal as a result of incubation with the indicated IRM compounds compared to a control in which the genetically modified cells were incubated in vehicle without IRM compound.

A compound was identified as increasing cellular activity mediated through a given TLR if it induced at least a two-fold increase in NFκB-induced luciferase signal compared to the control. A compound is further identified as selective between two TLRs if it modulates activity through a first TLR ($TLR_1 \geq 2 \times control$), does not modulate (i.e., substantially change) activity mediated through the second TLR ($TLR_2 \leq 2 \times control$), and increases activity mediated by the first TLR by at least two-fold more than it increases activity mediated by the second TLR ($TLR_1 \geq 2 \times TLR_2$). The assay identified TLR7-selective compounds (i.e., compounds that modulate TLR7-mediated activity, but not TLR8-mediated activity), TLR8-selective compounds (i.e., compounds that modulate TLR8-mediated activity, but not TLR7-mediated activity), and compounds that modulate cellular activity through both TLR7 and TLR8.

Compounds listed in Table 1 are compounds, in addition to some of the compounds shown in Example 1 (Table 5), that have been identified as being TLR8-selective compounds—in this case, compounds that, in the assay of Example 1, modulate cellular activity mediated through TLR8, but do not modulate cellular activity through TLR7.

TABLE 1

| Compound Name | Reference |
| --- | --- |
| N-{4-[4-amino-2-(2-methoxyethyl)-1H-imidazo[4,5-c]quinolin-1-yl]butyl}quinoline-3-carboxamide | U.S. Pat. No. 2003/0144283 Example 182 |
| N-{4-[4-amino-2-(2-methoxyethyl)-1H-imidazo[4,5-c]quinolin-1-yl]butyl}quinoxaline-2-carboxamide | U.S. Pat. No. 2003/0144283 Example 183 |
| N-[4-(4-amino-2-propyl-1H-imidazo[4,5-c]quinolin-1-yl)butyl]morpholine-4-carboxamide | U.S. Pat. No. 6,541,485[#] |

[#]This compound is not specifically exemplified but can be readily prepared using the synthetic methods disclosed in the cited reference.

Compounds listed in Table 2 are compounds, in addition to some of the compounds shown in Example 1 (Table 5), that have been identified as being TLR7-selective compounds—in this case, compounds that, in the assay of Example 1, modulate cellular activity mediated through TLR7, but do not modulate cellular activity through TLR8.

TABLE 2

| Compound Name | Reference |
| --- | --- |
| $N^1$-{4-[4-amino-2-(2-methoxyethyl)-6,7,8,9-tetrahydro-1H-imidazo[4,5-c]quinolin-1-yl]butyl}-4-fluoro-1-benzenesulfonamide | U.S. Pat. No. 6,331,539 Example 14 |
| $N^1$-[4-(4-amino-2-(2-methoxyethyl)-1H-imidazo[4,5-c]quinolin-1-yl)butyl]-4-fluoro-1-benzenesulfonamide | U.S. Pat. No. 6,331,539 Example 121 |
| N-[4-(4-amino-2-propyl-1H-imidazo[4,5-c]quinolin-1-yl)butyl]methanesulfonamide | U.S. Pat. No. 6,677,349 Example 235 |

TABLE 2-continued

| Compound Name | Reference |
| --- | --- |
| N-{3-[4-amino-2-(2-methoxyethyl)-1H-imidazo[4,5-c]quinolin-1-yl]-2,2-dimethylpropyl}benzamide | U.S. Pat. No. 2003/0144283 Example 190 |
| N-(2-{2-[4-amino-2-(2-methoxyethyl)-1H-imidazo[4,5-c]quinolin-1-yl]ethoxy}ethyl)-N-methylmethanesulfonamide | U.S. Pat. No. 6,683,088 Example 3 |
| N-(2-{2-[4-amino-2-(2-methoxyethyl)-6,7,8,9-tetrahydro-1H-imidazo[4,5-c]quinolin-1-yl]ethoxy}ethyl)benzamide | U.S. Pat. No. 6,660,747 Example 6 |
| N-[4-(4-amino-2-methyl-1H-imidazo[4,5-c]quinolin-1-yl)butyl]cyclopentanecarboxamide | U.S. Pat. No. 2003/0144283 Example 201 |
| 1-[4-(1,1-dioxidoisothiazolidin-2-yl)butyl]-2-(2-methoxyethyl)-1H-imidazo[4,5-c]quinolin-4-amine | U.S. Pat. No. 6,677,349 Example 266 |
| 2-methyl-1-[5-methylsulfonyl)pentyl-6,7,8,9-tetrahydro-1H-imidazo[4,5-c]quinolin-4-amine | U.S. Pat. No. 6,667,312 Example 75 |
| N-{2-[4-amino-2-(ethoxymethyl)-6,7-dimethyl-1H-imidazo[4,5-c]pyridin-1-yl]-1,1-dimethylethyl}-N'-cyclohexylurea | U.S. Pat. No. 6,545,017# |
| N-[2-(4-amino-2-ethyl-1H-imidazo[4,5-c]quinolin-1-yl)-1,1-dimethylethyl]benzamide | U.S. Pat. No. 2003/0144283# |
| N-[3-(4-amino-2-butyl-1H-imidazo[4,5-c]quinolin-1-yl)-2,2-dimethylpropyl]methanesulfonamide | U.S. Pat. No. 6,677,349# |
| 1-[6-(methanesulfonyl)hexyl]-6,7-dimethyl-2-propyl-1H-imidazo[4,5-c]pyridin-4-amine | U.S. Pat. No. 2004/0010007 Example 91 |
| 6-(4-amino-2-propyl-1H-imidazo[4,5-c]quinolin-1-yl)-N-methoxy-N-methylhexamide | U.S. Ser. No. 60/524961 Example 19 |
| 1-[2,2-dimethyl-3-(methylsulfonyl)propyl]-2-(ethoxymethyl)-1H-imidazo[4,5-c]quinolin-4-amine | U.S. Pat. No. 6,667,312# |
| N'-[4-(4-amino-2-methyl-1H-imidazo[4,5-c]quinolin-1-yl)butyl]-N-methyl-N-phenylurea | U.S. Pat. No. 6,541,485# |
| 1-{3-[4-amino-1-(2-methylpropyl)-1H-imidazo[4,5-c]quinolin-8-yl]phenyl}ethanone | U.S. Ser. No. 10/739787 Example 120 |
| 7-(4-amino-2-propyl-1H-imidazo[4,5-c]quinolin-1-yl)-2-methylheptan-2-ol | U.S. Pat. No. 4,689,338# |
| N-methyl-4-(4-amino-2-ethyl-1H-imidazo[4,5-c]quinolin-1-yl)butane-1-sulfonamide | U.S. Ser. No. 60/533465 Example 4 |
| N-(4-methoxybenzyl)-4-(4-amino-2-ethyl-1H-imidazo[4,5-c]quinolin-1-yl)butane-1-sulfonamide | U.S. Ser. No. 60/533465 Example 5 |
| N-{2-[4-amino-2-(ethoxymethyl)-6,7-dimethyl-1H-imidazo[4,5-c]pyridin-1-yl]-1,1-dimethylethyl}methanesulfonamide | U.S. Pat. No. 6,525,064# |
| 2-ethoxymethyl-1-(3-methoxypropyl)-7-(5-hydroxymethylpyridin-3-yl)-1H-imidazo[4,5-c]quinolin-4-amine | U.S. Ser. No. 10/739787 Example 167 |
| 1-[(2,2-dimethyl-1,3-dioxolan-4-yl)methyl]-2-(ethoxymethyl)-7-(pyridin-3-yl)-1H-imidazo[4,5-c]quinolin-4-amine | U.S. Ser. No. 10/739787 Example 159 |
| 4-[3-(4-amino-6,7-dimethyl-2-propyl-1H-imidazo[4,5-c]pyridin-1-yl)propane-1-sulfonyl]-benzoic acid ethyl ester | U.S. Pat. No. 2004/0010007 Example 99 |
| 2-butyl-1-{2-[2-(methylsulfonyl)ethoxy]ethyl}-1H-imidazo[4,5-c]quinolin-4-amine | U.S. Ser. No. 60/526772 Example 2 |
| N-(2-{4-amino-2-ethoxymethyl-7-[6-(methanesulfonylamino)hexyloxy]-1H-imidazo[4,5-c]quinolin-1-yl}-1,1-dimethylethyl)methanesulfonamide | U.S. Ser. No. 60/508634 Example 45 |
| N-(6-{[4-amino-2-ethoxymethyl-1-(2-methanesulfonylamino-2-methylpropyl)-1H-imidazo[4,5-c]quinolin-7-yl]oxy}hexyl)acetamide | U.S. Ser. No. 60/508634 Example 46 |
| 1-[4-(1,1-dioxidoisothiazolidin-2-yl)butyl]-2-ethoxymethyl-7-(pyridin-3-yl)-1H-imidazo[4,5-c]quinolin-4-amine | U.S. Ser. No. 10/739787 Example 153 |
| 1-[4-(1,1-dioxidoisothiazolidin-2-yl)butyl]-2-ethoxymethyl-7-(pyridin-4-yl)-1H-imidazo[4,5-c]quinolin-4-amine | U.S. Ser. No. 10/739787 Example 154 |
| 1-[4-(1,1-dioxidoisothiazolidin-2-yl)butyl]-2-ethoxymethyl-7-phenyl-1H-imidazo[4,5-c]quinolin-4-amine | U.S. Ser. No. 10/739787 Example 152 |
| 2-(ethoxymethyl)-1-{[1-(methylsulfonyl)piperidin-4-yl]methyl}-7-(pyridin-3-yl)-1H-imidazo[4,5-c]quinolin-4-amine | U.S. Ser. No. 10/739787 Example 178 |

TABLE 2-continued

| Compound Name | Reference |
|---|---|
| 2-(ethoxymethyl)-1-[(1-isobutyrylpiperidin-4-yl)methyl]-7-(pyridin-3-yl)-1H-imidazo[4,5-c]quinolin-4-amine | U.S. Ser. No. 10/739787 Example 179 |
| 2-(ethoxymethyl)-1-{[1-(morpholin-4-ylcarbonyl)piperidin-4-yl]methyl}-7-(pyridin-3-yl)-1H-imidazo[4,5-c]quinolin-4-amine | U.S. Ser. No. 10/739787 Example 180 |
| Cyclopropanecarboxylic acid [3-(4-amino-2-propyl-1H-imidazo[4,5-c]quinolin-1-yl)propoxy]amide | U.S. Ser. No. 60/494605 Example 2 |
| Isopropylcarbamic acid 4-amino-2-(2-methoxyethyl)-1-propyl-1H-imidazo[4,5-c]quinolin-7-yl ester | U.S. Ser. No. 60/508634 Example 366 |
| Ethyl 4-(4-amino-2-propyl-1H-imidazo[4,5-c]quinolin-1-yl)butyrate | U.S. Ser. No. 60/524961 Example 38 |
| 1-[4-amino-2-ethyl-7-(pyridin-3-yl)-1H-imidazo[4,5-c]quinolin-1-yl]-2-methylpropan-2-ol | U.S. Ser. No. 10/739787 Example 143 |
| 1-{4-amino-2-ethyl-7-[5-(hydroxymethyl)pyridin-3-yl]-1H-imidazo[4,5-c]quinolin-1-yl}-2-methylpropan-2-ol | U.S. Ser. No. 10/739787 Example 144 |
| 1-{3-[4-amino-2-(2-methoxyethyl)-8-(pyridin-3-yl)-1H-imidazo[4,5-c]quinolin-1-yl]propyl}pyrrolidin-2-one | U.S. Ser. No. 10/739787 Example 188 |
| N-(2-{4-amino-2-ethoxymethyl-7-[6-(methanesulfonylamino)hexyloxy]-1H-imidazo[4,5-c]quinolin-1-yl}-1,1-dimethylethyl)acetamide | U.S. Ser. No. 60/508634 Example 49 |
| 1-{3-[4-amino-7-(3-hydroxymethylphenyl)-2-(2-methoxyethyl)-1H-imidazo[4,5-c]quinolin-1-yl]propyl}pyrrolidin-2-one | U.S. Ser. No. 10/739787 Example 185 |
| N-{4-[4-amino-2-ethoxymethyl-7-(pyridin-3-yl)-1H-imidazo[4,5-c]quinolin-1-yl]butyl}-N'-propylurea | U.S. Ser. No. 10/739787 Example 378 |
| N-{4-[4-amino-2-ethoxymethyl-7-(pyridin-3-yl)-1H-imidazo[4,5-c]quinolin-1-yl]butyl}butyramide | U.S. Ser. No. 10/739787 Example 372 |
| 5-(4-amino-2-propyl-1H-imidazo[4,5-c]quinolin-1-yl)-4,4-dimethylpentan-2-one | U.S. Ser. No. 60/524961 Example 36 |
| 1-cyclohexylmethyl-2-ethoxymethyl-7-(5-hydroxymethylpyridin-3-yl)-1H-imidazo[4,5-c]quinolin-4-amine | U.S. Ser. No. 10/739787 Example 439 |
| N,N-dimethyl-5-(4-amino-2-ethoxymethyl-1H-imidazo[4,5-c]quinolin-1-yl)pentane-1-sulfonamide | U.S. Ser. No. 60/533465 Example 17 |
| N-{3-[(4-amino-2-ethoxymethyl-1H-imidazo[4,5-c]quinolin-1-yl)amino]propyl}methanesulfonamide | U.S. Ser. No. 60/532191 Example 14 |
| N,N-dimethyl-4-(4-amino-2-ethoxymethyl-1H-imidazo[4,5-c]quinolin-1-yl)butane-1-sulfonamide | U.S. Ser. No. 60/533465 Example 11 |

This compound is not specifically exemplified but can be readily prepared using the synthetic methods disclosed in the cited reference.

Another embodiment is exemplified in Example 2, in which selective modulation between TLR6 and TLR7 was observed in genetically modified Namalwa cells by detecting TLR-mediated IFN-α1-induced transcription of a luciferase reporter. Results are shown in Table 6 and are expressed as fold induction of IFN-α1-induced luciferase signal, again with respect to a vehicle control.

A compound was identified as increasing cellular activity mediated through a given TLR if the compound induced at least a two-fold increase in IFN-α1-induced luciferase signal. A compound is further identified as selective between two TLRs if it modulates activity through a first TLR (TLR$_1 \geq 2\times$ control), does not modulate (i.e., substantially change) activity mediated through the second TLR (TLR$_2 \leq 2\times$control), and increases activity mediated by the first TLR by at least two-fold more than it increases activity mediated by the second TLR (TLR$_1 \geq 2\times$TLR$_2$). The assay identified TLR6-selective compounds (i.e., compounds that modulate TLR6-mediated activity, but not TLR7-mediated activity), TLR7-selective compounds (compounds that modulate TLR7-mediated activity, but not TLR6-mediated activity), and compounds that modulate cellular activity through both TLR6 and TLR7.

Compounds listed in Table 3 are compounds, in addition to some of the compounds shown in Example 2 (Table 6), that have been identified as being TLR6-selective compounds—in this case, compounds that, in the assay of Example 2, modulate cellular activity mediated through TLR6, but do not modulate cellular activity through TLR7.

TABLE 3

| Compound Name | Reference |
|---|---|
| N-[2-(4-amino-2-butyl-1H-imidazo[4,5-c]quinolin-1-yl)ethyl]-4-methylbenzenesulfonamide | U.S. Pat. No. 6,331,539 Example 23* |
| 1-[(1R-1-phenylethyl]1H-imidazo4,5-c][1,5]naphthyridin-4-amine | U.S. Pat. No. 6,194,425# |
| $N^6$-[4-(4-amino-1H-imidazo[4,5-c]quinolin-1-yl)butyl]-6-quinolinecarboxamide | U.S. Pat. No. 6,451,810 Example 21 |
| N-{4-[4-amino-2-(2-methoxyethyl)-6,7,8,9-tetrahydro-1H-imidazo[4,5-c]quinolin-1-yl]butyl}methanesulfonamide methanesulfonate | U.S. Pat. No. 6,331,539 Example 214* |
| 1-[4-(phenylsulfonyl)butyl]-1H-imidazo[4,5-c]quinolin-4-amine | U.S. Pat. No. 6,664,264 Example 7 |
| 2-(2-methoxyethyl)-1-[2-(3-phenylpropoxy)ethyl]-1H-imidazo[4,5-c]quinolin-4-amine | U.S. Pat. No. 6,670,372 Example 121 |
| 2-(ethoxymethyl)-1-{2-[(3-phenylprop-2-ynyl)oxy]ethyl}-1H-imidazo[4,5-c]quinolin-4-amine | U.S. Pat. No. 6,670,372 Example 122 |
| $N^1$-[4-(4-amino-2-butyl-1H-imidazo[4,5-c]quinolin-1-yl)butyl]-3-nitro-1-benzenesulfonamide | U.S. Pat. No. 6,331,539 Example 7 |

*Examples 23 and 214 the trifluoroacetate salt. The salt is converted to the listed compound using conventional methods.
This compound is not specifically exemplified but can be readily prepared using the synthetic methods disclosed in the cited reference.

The methods of the present invention can include modulating cellular activity mediated by any TLR. The structural genes of ten human TLRs have been cloned and sequenced. Thus, the structural gene of any one of the ten human TLRs may be introduced into a host cell to provide a genetically modified cell line for use in an assay in a method according to the present invention. In some embodiments, the structural gene of a particular TLR may be cloned into a human cell line such as, for example, HEK293 cells, Namalwa cells, mouse RAW cells, or fibroblasts. HEK293 cells and Namalwa cells genetically modified in this way may be used to detect modulation of cellular activities mediated by the cloned TLR, as described above.

In other embodiments, the particular TLR-mediated cellular activity detected in the assay may be determined by the identity of a TLR naturally expressed by a cell and the natural biological activity of that cell in response to activation of the TLR. For example, human monocytes naturally express TLR8 and, when contacted with a TLR8 agonist, respond by, for example, producing the cytokine IL-12. Thus, IL-12 production by monocytes is just one example of a TLR8-mediated cellular activity that could be assayed as part of a method according to the present invention. Other cell types express TLRs in a generally characteristic profile. In many cases, the biological response of the cells to exposure to an agonist of a particular TLR is known or can be readily determined. Thus, one of skill in the art can select an appropriate cell population having a detectable biological response to a particular TLR for use in an assay to detect cellular activity mediated by any TLR.

In some embodiments, the compound can modulate two or more separate TLR-mediated cellular activities, but modulate one activity to a different extent than another activity. For example, a compound may modulate two different TLR-mediated cellular activities in an opposite manner, i.e., increase one cellular activity and inhibit the other activity. Alternatively, a compound may modulate two TLR-mediated cellular activities in the same manner (i.e., either increase or inhibit both activities), but modulate one activity to greater extent than the other activity. Alternatively, the compound may detectably modulate one TLR-mediated cellular activity, but substantially fail to modulate a second TLR-mediated cellular activity to a detectable extent.

The present invention also provides compounds identified according to the method described above. Unless otherwise indicated, reference to a compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers.

The method described above can employ any assay that detects any modulation of any cellular activity mediated by any TLR. Accordingly, the methods described above can be a powerful tool for identifying a broad spectrum of compounds that selectively modulate one or more TLR-mediated activities. The compounds thus identified may be incorporated into a pharmaceutical composition. Such pharmaceutical compositions are described in greater detail below.

In another aspect, the present invention provides a method of identifying a target compound having a particular TLR modulation profile. Generally, the method includes selecting a target TLR modulation profile; determining the TLR modulation profile of a test compound; and identifying the test compound as a target compound if the TLR modulation profile of the test compound conforms to the target TLR modulation profile.

As used herein, a TLR modulation profile includes representative effects characteristic of modulating at least one TLR-mediated cellular activity. In the context of a target TLR modulation profile, the profile may include one or more desired modulated TLR-mediated activities. For example, one of skill in the art might recognize that a particular condition can be treated effectively by administering a drug that, for example, increases a particular TLR-mediated cellular activity (e.g., production of, for example, IL-12 or IFN-α).

In other cases, the target TLR modulation profile might include effects relating to two or more TLR-mediated cellular activities. For example, a particular condition might be treated effectively by administering a drug that, for example, increases a cellular activity mediated by one TLR, but does not modulate cellular activity mediated by a second TLR. In yet another example, a particular condition might be treated effectively by administering a drug that, for example, increases a cellular activity mediated by one TLR and inhibits a cellular activity mediated by a second TLR.

A target TLR modulation profile may contain as much or as little information as is known and/or required to provide a desired result. In some cases, the relevant portion of a target TLR modulation profile may include effects of cellular activity mediated by a single TLR, e.g., TLR7, without regard to any effects of biological activity mediated by any other TLR, e.g., TLR6 or TLR8. This may be so because of certain factors relating to the condition being treated or the target cell population whose biological activity is being modulated. Such factors include but are not limited to the identity of TLRs expressed by target cells; the relative levels of expression of the TLRs expressed by the target cells; the location of the target cells—in vitro, in vivo, and if in vivo, the tissue or organ in which the target cells are located; and the general state of the immune system (e.g., suppressed, compromised, stimulated), if present. For example, plasmacytoid dendritic cells (pDCs) express TLR7, but exhibit minimal, if any, expression of TLR8. Consequently, TLR8-mediated cellular activity may be largely irrelevant when considering a target TLR modulation profile for, e.g., activating pDCs.

The TLR modulation profile of a test compound may be determined in any suitable manner. One method of determining the TLR modulation profile of a compound is to perform one or more assays such as, for example, the assays described in detail above to determine whether a test compound detectably modulates the cellular activity mediated by a particular TLR. Alternatively, certain compounds are already known to be agonists of one or more TLRs. For example, certain small molecule IRM compounds are known to be agonists of one or more of TLR6, TLR7, and TLR8. Certain oligonucleotide IRM compounds are known to be agonists of TLR9. In some cases, at least a portion of a TLR modulation profile of a test compound may be derived from clinical or anecdotal observation of effects of administering the compound to a subject when, for example, the observed effects may be correlated to a particular TLR-mediated cellular activity.

The TLR modulation profile of a test compound may contain as much or as little information as is desired for comparison with the target TLR modulation profile. The extent of the information desired for the TLR modulation profile of a test compound may depend, at least in part, on a number of factors such as, for example, the factors listed above with respect to the determining the target TLR modulation profile.

Identifying a test compound as having a particular target TLR modulation profile involves comparing the TLR modulation profile of the test compound with the target TLR modulation profile. In some cases, the target TLR modulation profile and the TLR modulation profile of the test compound may include the same TLR-mediated cellular activities, each modulated in the same direction and to the same extent. In such cases, the test compound can be readily identified as conforming to the target TLR modulation profile.

In certain cases in which the target TLR modulation profile and the TLR modulation profile of the test compound differ to some extent, the test compound may still be identified as conforming to the desired TLR modulation profile. For example, the test compound might modulate a particular TLR-mediated cellular activity that, for the purposes of the target TLR modulation profile, has little if any relevance. For example, if a target TLR modulation profile is determined for the activation of pDCs, which express TLR7 but not TLR8, a test compound that modulates TLR7-mediated cellular activity, but does not modulate TLR8-mediated cellular activity may conform to the target TLR modulation profile. A test compound that modulates both TLR7-mediated and TLR8-mediated cellular activities also may be considered to conform to the target TLR modulation profile, because the compound's ability to modulate TLR8-mediated cellular activity in addition to TLR7-mediated cellular activity may not be relevant for a particular application.

Alternatively, in some embodiments, the method of the present invention can include cases in which the target TLR modulation profile includes one or more TLR-mediated cellular activities that are not detectably modulated by a test compound. Different portions of the target TLR modulation profile may be deemed to be of primary and secondary importance, so that a test compound may be identified as conforming to the target TLR modulation profile if the compound modulates the primary TLR-mediated cellular activity in accordance with the target TLR modulation profile, even if the compound does not modulate the secondary TLR-mediated cellular activity in precise accordance with the target TLR modulation profile. For example, a target TLR modulation profile may include, primarily, increasing TLR8-mediated cellular activity and, secondarily, decreasing TLR7-mediated cellular activity. A test compound that adequately increases TLR8-mediated cellular activity, but does not modulate TLR7-mediated cellular activity may, in certain circumstances, be considered to conform to the target TLR modulation profile if, for example, the benefits of increasing the TLR8-mediated cellular activity sufficiently outweigh any drawbacks of not inhibiting TLR7-mediated biological activity.

The target TLR modulation profile may vary according to the specific applications for which compounds identified as conforming to the target TLR modulation profile are to be used. For example, treatment of certain viral infections may benefit from administration of a compound that increases TLR7-mediated cellular activity. Such treatments may, for example, induce production of Type I interferons and activate certain antigen presenting cells (APCs). Alternatively, treatment of certain types of tumors may benefit from using a compound that increases TLR8-mediated cellular activity. Such TLR8 agonists may induce immune system activity localized to the area to which the TLR8 agonist is administered including, for example, induction of IL-12 secretion, activation of macrophages, infiltration of the treated area by macrophages, and a strong inflammatory response. In still other embodiments, treatment of some tumors may benefit from administration of a compound that increases both TLR7-mediated and TLR8-mediated cellular responses. Such treatment may induce Type I interferon production and IL-12 production, which together synergistically enhance IFN-γ production. IFN-γ production may help facilitate an immune response against malignant cancers such as, for example, melanoma and renal cell carcinoma.

The present invention also provides compounds identified as target compounds according to the method described above. The method described above can employ any suitable target TLR modulation profile, incorporating information relating to the modulation of any number of the known TLRs. Accordingly, the methods described above can be a powerful tool for identifying a broad spectrum of compounds that conform to a particular target TLR modulation profile. The compounds thus identified may be incorporated into a pharmaceutical composition. Such pharmaceutical compositions are described in greater detail below.

In another aspect, the present invention provides a method of selectively modulating cells of the immune system. Generally, the method includes identifying a first immune system cell population and a second immune system cell population; selecting a compound that modulates a TLR-mediated cellular activity of the first cell population to a different extent than it modulates a TLR-mediated cellular activity of the second cell population; and contacting cells of the immune system with the selected compound in an amount effective to modulate at least one of the cell populations.

In some embodiments, at least one cell population comprises monocytes. In alternative embodiments, at least one cell population comprises macrophages. In other alternative embodiments, at least one cell population comprises Langerhans cells. In other alternative embodiments, at least one cell population comprises dendritic cells such as, for example, plasmacytoid dendritic cells or monocytes-derived dendritic cells. In other alternative embodiments, at least one cell population comprises Natural Killer cells. In other alternative embodiments, at least one cell population comprises polymorphonuclear cells such as, for example, neutrophils, basophils, or eosinophils. In other alternative embodiments, at least one cell population comprises B lymphocytes. In other alternative embodiments, at least one cell population comprises T lymphocytes. In still other alternative embodiments, at least one cell population comprises a combination of two or more of any of the foregoing cell types.

The immune system includes various populations of cells, each population carrying out one or more functions that facilitate mounting an effective immune response against an immunological challenge. The various populations of cells populate different areas of the body such as, for example, the blood, skin, bone marrow, thymus, lymphatic system, and interstitial areas. The various populations of immune cells also express the various TLRs to different extents—i.e., possess different TLR expression profiles. For example, monocytes express relatively large amounts of TLR2 and TLR4, and also show significant levels of, for example, TLR1 and TLR8 expression, and low levels of TLR7 expression. B lymphocytes exhibit relatively high expression of TLR1, TLR6, and TLR10, but also express, for example, TLR7 and TLR9. Plasmacytoid dendritic cells (pDCs) predominantly express TLR9, but also express some TLR1, TLR6, TLR7, and TLR10.

With the discovery that some compounds may modulate cellular activity mediated by one TLR, but not modulate cellular activity mediated by another TLR, the present invention provides means by which one can selectively modulate cells of the immune system. The selective modulation may take the form of modulating one population of immune cells while leaving the activity of another population of immune cells substantially unmodulated (i.e., qualitative or "on-off" modulation). Alternatively, the selective modulation may involve modulating the TLR-mediated cellular activity of two or more immune cell populations to varying degrees (i.e., quantitative modulation).

In certain embodiments, the methods of the present invention include determining the TLR expression profile of the first cell population and the TLR expression profile of the second cell population. The TLR expression profile may be determined by any suitable method including but not limited to detection of TLR expression such as by PCR analysis, pulse-chase analysis of TLR protein synthesis, and labeling TLRs using TLR-specific antibodies for analyses such as, but not limited to, immunohistochemistry, Western blots, or flow cytometry.

The selective modulation of immune cells may include detectably activating the cells or detectably inhibiting the cells. The cells of the immune system may be selectively modulated either in vitro or in vivo. In vitro selective modulation may include collecting a sample of immune cells from a subject, culturing the collected immune cells in vitro, and adding the selected compound to the cell culture. The sample of immune cells collected from the subject may be a heterogeneous sample of cells, i.e., the sample may include cells of more than one population of immune cells. After the cells have been selectively modulated, the treated cells may be reintroduced into the subject, thereby providing prophylactic or therapeutic treatment. Alternatively, cells selectively modulated in vitro may have diagnostic utility.

FIG. 1 shows the TLR-selective activation of myeloid dendritic cells (mDCs) in vitro. From each of two donors, mDCs were activated by a TLR 7/8 agonist (IRM16) and a TLR8-selective compound (IRM9), but were not activated by a TLR7-selective compound (IRM36) or a TLR9 agonist (CpG). The observation that mDC activation is TLR8-selective—at least with respect to TLR7-mediated cellular activity—is independent of the particular TLR8-selective agonist or TLR7-selective agonist used (Example 3, Table 4).

Figure 2:
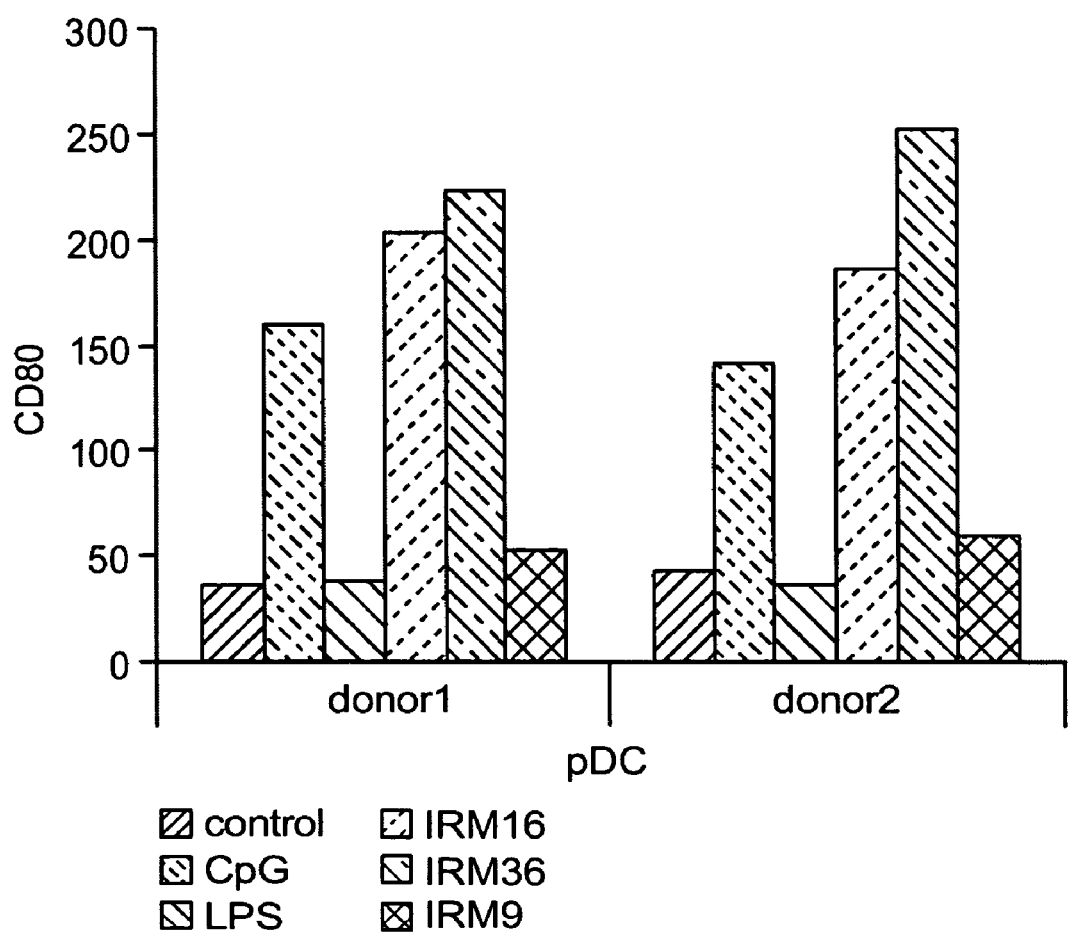
FIG. 2 is a bar graph showing selective activation of plasmacytoid dendritic cells.

FIG. 2 shows the TLR-selective activation of plasmacytoid dendritic cells (pDCs) in vitro. From each of two donors, pDCs were activated by a TLR 7/8 agonist (IRM16), a TLR7-selective compound (IRM36), and a TLR9 agonist (CpG), but were not activated by a TLR8-selective compound (IRM9).

In some embodiments, cells selectively modulated in vitro may be genetically modified rather than collected from a subject. Such cells may have utility as experimental tools, such as, for example, further elucidating TLR-mediated cellular activity.

In vivo selective modulation may include administering the selected compound to a subject. The selected compound may be administered in any suitable manner including but not limited to topical, injection (e.g., intravenous, subcutaneous, intraperitoneal, intradermal), inhalation, ingestion, transdermal, or transmucosal delivery.

The particular amount of the selected compound effective for selectively modulating immune cells in a subject may depend, at least in part, on one or more factors. Such factors include, but are not limited to, the particular compound being administered, the state of the subject's immune system (e.g., suppressed, compromised, stimulated); the identity and location of the cells being modulated; the route of administering the compound; the TLR expression profile of the cells being modulated; and the desired result (e.g., prophylactic or therapeutic treatment). Accordingly, it is not practical to set forth generally the amount of compound effective for selectively modulating immune cells for all applications. Those of ordinary skill in the art, however, can readily determine the appropriate amount with due consideration of such factors.

An amount of the selected compound effective to selectively modulate cells of the immune system is an amount sufficient to cause the targeted cell population or populations (e.g., monocytes, macrophages, dendritic cells, B cells, T cells, etc.) to alter at least one TLR-mediated cellular activity (e.g., cytokine production).

The precise amount of compound necessary to alter at least one TLR-mediated cellular activity may vary according to factors known in the art, but in certain embodiments the amount can be a dose of from about 100 ng/kg to about 50 mg/kg, for example, from about 10 µg/kg to about 5 mg/kg. In other embodiments, the amount may be an amount sufficient to provide a final concentration of from about 0.001 µM to about 100 µM of the selected compound in a suitable solution. The minimum amount of the selected compound may vary, dependent upon the factors described above, but may be, in certain embodiments, 0.001 µM, 0.003 µM, 0.01 µM, 0.03 µM, 0.1 µM, 0.3 µM, 1.0 µM, 3.0 µM, or 10 µM. Similarly, the maximum amount of the selected compound may vary, dependent upon the factors described above, but may be, in certain embodiments, 100 µM, 30 µM, 10 µM, 3 µM, 1.0 µM, 0.3 µM, or 0.1 µM.

As noted above, a compound that selectively modulates a TLR-mediated cellular activity may be incorporated into a pharmaceutical composition. Such compositions may be useful for treatment of conditions treatable by selectively modulating one or more TLR-mediated cellular activities.

A TLR-selective compound can be administered as the single therapeutic agent in a treatment regimen. Alternatively, a compound of the invention may be administered in combination with another TLR-selective compound or with one or more active agents such as, for example, additional IRM compounds, immunogens, adjuvants, antivirals, antibiotics, anticancers, etc.

Accordingly, the present invention also provides a method of treating a condition treatable by selective modulation of a plurality of TLR-mediated cellular activities. Generally, the method includes identifying a target TLR modulation profile effective for treatment of the condition; selecting an IRM compound having a TLR modulation profile that conforms to the target TLR modulation profile; and administering to the subject an amount of the IRM compound effective for treating the condition.

In some embodiments, the target TLR modulation profile includes TLR6-mediated cellular activity such as, for example, modulation of TLR6-mediated cellular activity. In certain such embodiments, the target modulation profile includes substantially no modulation of TLR7-mediated cellular activity.

In some embodiments, the IRM compound TLR modulation profiles includes TLR6-mediated cellular activity such as, for example, modulation of TLR6-mediated cellular activity. In certain such embodiments, the IRM compound TLR modulation profile includes substantially no modulation of TLR7-mediated cellular activity.

In some embodiments, the target TLR modulation profile includes TLR7-mediated cellular activity such as, for example, modulation of TLR7-mediated cellular activity. In certain such embodiments, the target TLR modulation profile includes substantially no modulation of TLR6-mediated cellular activity. In certain alternative embodiments, the target TLR modulation profile includes substantially no modulation of TLR8-mediated cellular activity.

In some embodiments, the IRM compound TLR modulation profile includes TLR7-mediated cellular activity such as, for example, modulation of TLR7-mediated cellular activity. In certain such embodiments, the IRM compound TLR modulation profile includes substantially no modulation of TLR6-mediated cellular activity. In certain alternative embodiments, the IRM compound TLR modulation profile includes substantially no modulation of TLR8-mediated cellular activity.

In some embodiments, the target TLR modulation profile includes TLR8-mediated cellular activity such as, for example, modulation of TLR8-mediated cellular activity. In certain such embodiments, the target TLR modulation profile includes substantially no modulation of TLR7-mediated cellular activity.

In some embodiments, the IRM compound TLR modulation profile includes TLR8-mediated cellular activity such as, for example, modulation of TLR8-mediated cellular activity. In certain such embodiments, the IRM compound TLR modulation profile includes substantially no modulation of TLR7-mediated cellular activity.

In some embodiments, the target TLR modulation profile includes TLR9-mediated cellular activity such as, for example, modulation of TLR9-mediated cellular activity.

In some embodiments, the IRM compound TLR modulation profile includes TLR9-mediated cellular activity such as, for example, modulation of TLR9-mediated cellular activity.

In some embodiments, the IRM compound is a TLR6-selective compound. In alternative embodiments, the IRM compound is a TLR7-selective compound. In other alternative embodiments, the IRM compound is a TLR8-selective compound. In still other alternative embodiments, the IRM compound is a TLR9-selective compound.

Treating a condition may involve either prophylactic or therapeutic treatment. As used herein, prophylactic treatment refers to treatment initiated before the onset of symptoms or signs of the condition. Thus, prophylactic treatments generally are designed to: (1) reduce the likelihood that the subject receiving the treatment will acquire the condition, (2) reduce the severity of the condition, acquired, or (3) both. As used herein, therapeutic treatment refers to treatment initiated after the onset of symptoms or signs of a condition. Thus, therapeutic treatments are designed to limit or reduce progression of the condition. In some cases, therapeutic treatments can result in reversal of the condition, even to the point of complete resolution.

Identifying the target TLR-mediated cellular activity profile may involve determining which immune system cell population or populations might be well-suited for providing prophylactic or therapeutic treatment of the condition, then determining which TLR-mediated cellular activities of the identified cell populations might be modulated to provide the desired treatment.

The TLR modulation profile of the IRM compound may be determined by performing one or more assays designed to detect modulation of TLR-mediated cellular activities. Alternatively, the TLR modulation profile of the IRM compound may be determined by clinical or even anecdotal observation.

Selecting an IRM compound having a TLR modulation profile that conforms to the target TLR modulation profile involves the same considerations described above relating to assays for identifying a target compound having a particular TLR modulation profile.

Conditions that may be treated by administering a TLR-selective compound include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or. Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacte-*

*rium, Campylobacter, Vibrio, Serratia, Providencia, Chromobacterium, Brucella, Yersinia, Haemophilus,* or *Bordetella;*

(c) other infectious diseases, such chlamydia, fungal diseases including but not limited to candidiasis, aspergillosis, histoplasmosis, cryptococcal meningitis, or parasitic diseases including but not limited to malaria, pneumocystis camii pneumonia, leishmaniasis, cryptosporidiosis, toxoplasmosis, and trypanosome infection; and (d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, renal cell carcinoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing would healing, including chronic wounds).

Additionally, a TLR-selective compound may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; autologous vaccines; recombinant proteins; glycoproteins; peptides; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Certain TLR-selective compounds may be particularly helpful in individuals having compromised immune function. For example, certaincompounds may be used for treating the opportunistic infections and tumors that occur after suppression of cell mediated immunity in, for example, transplant patients, cancer patients and HIV patients.

In some embodiments, the TLR-selective compound can be a known IRM compound including the small organic IRM molecules described above, or the purine derivatives, small heterocyclic compounds, amide derivatives, and oligonucleotide sequences described above. Alternatively, the TLR-selective compound employed in some embodiments of the present invention may be a compound identified as TLR-selective compound by any suitable method of identifying a TLR-selective compound, including some of the methods according to the present invention.

The TLR-selective compound may be provided in any formulation suitable for administration to a subject. Suitable types of formulations are described, for example, in U.S. Pat. Nos. 5,736,553; 5,238,944; 5,939,090; 6,365,166; 6,245,776; 6,486,186; European Patent No. EP 0 394 026; and U.S. Patent Publication No. 2003/0199538. The TLR-selective compound may be provided in any suitable form including but not limited to a solution, a suspension, an emulsion, or any form of mixture. The TLR-selective compound may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives such as, for example, adjuvants, skin penetration enhancers, colorants, fragrances, flavorings, moisturizers, thickeners, and the like.

A formulation may be administered in any suitable manner such as, for example, non-parenterally or parenterally. As used herein, non-parenterally refers to administration through the digestive tract, including by oral ingestion. Parenterally refers to administration other than through the digestive tract such as, for example, intravenously, intramuscularly, transdermally, subcutaneously, transmucosally (e.g., by inhalation), or topically.

In some embodiments, a TLR-selective compound can be administered to a subject in a formulation of, for example, from about 0.0001% to about 10% (unless otherwise indicated, all percentages provided herein are weight/weight with respect to the total formulation) to the subject, although in some embodiments the TLR-selective compound may be administered using a formulation that provides the TLR-selective compound in a concentration outside of this range. In certain embodiments, the method includes administering to a subject a formulation that includes from about 0.01% to about 1% TLR-selective compound, for example, a formulation that includes from about 0.1% to about 0.5% TLR-selective compound.

An amount of a TLR-selective compound effective for treating a condition is an amount sufficient to provide the desired therapeutic or prophylactic benefit. The precise amount of TLR-selective compound for treating a condition will vary according to factors known in the art including but not limited to the condition, the physical and chemical nature of the TLR-selective compound, the nature of the carrier, the intended dosing regimen, the state of the subject's immune system (e.g., suppressed, compromised, stimulated), the method of administering the TLR-selective compound, and the species to which the formulation is being administered. Accordingly, it is not practical to set forth generally the amount that constitutes an amount of TLR-selective compound effective for treating a condition for all possible applications. Those of ordinary skill in the art, however, can readily determine the appropriate amount with due consideration of such factors.

In some embodiments, the methods of the present invention include administering sufficient TLR-selective compound to provide a dose of, for example, from about 100 ng/kg to about 50 mg/kg to the subject, although in some embodiments the methods may be performed by administering the TLR-selective compound in concentrations outside this range. In some of these embodiments, the method includes administering sufficient TLR-selective compound to provide a dose of from about 10 µg/kg to about 5 mg/kg to the subject, for example, a dose of from about 100 µg/kg to about 1 mg/kg.

The dosing regimen may depend at least in part on many factors known in the art including but not limited to the condition, the physical and chemical nature of the TLR-selective compound, the nature of the carrier, the amount of TLR-selective compound being administered, the state of the subject's immune system (e.g., suppressed, compromised, stimulated), the method of administering the TLR-selective compound, and the species to which the formulation is being administered. Accordingly it is not practical to set forth generally the dosing regimen effective for treating a condition for all possible applications. Those of ordinary skill in the art, however, can readily determine the appropriate amount with due consideration of such factors.

In some embodiments of the invention, the TLR-selective compound may be administered, for example, from a single dose to multiple doses per day, although in some embodiments the methods of the present invention may be performed by administering the TLR-selective compound at a frequency outside this range. In certain embodiments, the TLR-selective compound may be administered from about once per week to about three times per day such as, for example, administering the TLR-selective compound once per day.

The organism treated for a condition may be a plant or animal, particularly a vertebrate. Preferably the organism treated for the disorder is a mammal, such as, but not limited to, human, rodent, dog, cat, pig, sheep, goat, or cow.

In some embodiments, the selected compound can be a known IRM compound including the small organic IRM molecules described in detail below, or the purine derivatives, small heterocyclic compounds, amide derivatives, and oligonucleotide sequences described above. Alternatively, the selected compound may be a compound capable of selectively modulating at least one TLR-mediated cellular activity, identified by any suitable method of identifying such compounds, including some of the methods according to the present invention.

IRM compounds suitable for use in the invention include compounds having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamido substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines.

In certain embodiments, the IRM compound may be a substituted imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

As used herein, a substituted imidazoquinoline amine refers to an amide substituted imidazoquinoline amine, a sulfonamide substituted imidazoquinoline amine, a urea substituted imidazoquinoline amine, an aryl ether substituted imidazoquinoline amine, a heterocyclic ether substituted imidazoquinoline amine, an amido ether substituted imidazoquinoline amine, a sulfonamido ether substituted imidazoquinoline amine, a urea substituted imidazoquinoline ether, a thioether substituted imidazoquinoline amines, or a 6-, 7-, 8-, or 9-aryl or heteroaryl substituted imidazoquinoline amine. As used herein, substituted imidazoquinoline amines specifically and expressly exclude 1-(2-methylpropyl)-1H-imidazo[4,5-c]quinolin-4-amine and 4-amino-act-dimethyl-2-ethoxymethyl-1H-imidazo[4,5-c]quinolin-1-ethanol.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention.

TABLE 4

| Compound | Chemical Name | Reference |
| --- | --- | --- |
| IRM1 | 2-(ethoxymethyl)-1-(2-methylpropyl)-1H-imidazo[4,5-c]quinolin-4-amine | U.S. Pat. No. 5,389,640 Example 40 |
| IRM2 | 2-methyl-1-[2-(3-pyridin-3-ylpropoxy)ethyl]-1H-imidazo[4,5-c]quinolin-4-amine | WO 02/46193 Example 34 |
| IRM3 | N-(2-{2-[4-amino-2-(2-methoxyethyl)-1H-imidazo[4,5-c]quinolin-1-yl]ethoxy}ethyl)-N-methylcyclohexanecarboxamide | U.S. Ser. No. 10/165,449 Example 73 |
| IRM4 | 1-[2-(benzyloxy)ethyl]-2-methyl-1H-imidazo[4,5-c]quinolin-4-amine | WO 02/46189 Example 127 |

TABLE 4-continued

| Compound | Chemical Name | Reference |
|---|---|---|
| IRM5 | N-{8-[4-amino-2-(2-methoxyethyl)-1H-imidazo[4,5-c]quinolin-1-yl]octyl}-N'-phenylurea | U.S. Ser. No. 10/028255 Example 148 |
| IRM6 | 2-butyl-1-[5-(methylsulfonyl)pentyl]-1H-imidazo[4,5-c]quinolin-4-amine | WO 02/46192 Example 11 |
| IRM7 | N-{3-[4-amino-2-(2-methoxyethyl)-1H-imidazo[4,5-c]quinolin-1-yl]propyl}-4-methylbenzenesulfonamide | U.S. Pat. No. 6,331,539# |
| IRM8 | N-[4-(4-amino-2-ethyl-1H-imidazo[4,5-c]quinolin-1-yl)butyl]cyclohexanecarboxamide | U.S. Ser. No. 10/027218 Example 204 |
| IRM9 | 2-propylthiazolo[4,5-c]quinolin-4-amine | U.S. Pat. No. 6,110,929 Example 12 |
| IRM10 | $N^1$-[2-(4-amino-2-butyl-1H-imidazo[4,5-c][1,5]naphthyridin-1-yl)ethyl]-2-amino-4-methylpentanamide | U.S. Pat. No. 6,194,425 Example 102 |
| IRM11 | $N^1$-[4-(4-amino-1H-imidazo[4,5-c]quinolin-1-yl)butyl]-2-phenoxybenzamide | U.S. Pat. No. 6,451,810 Example 14 |
| IRM12 | $N^1$-[2-(4-amino-2-butyl-1H-imidazo[4,5-c]quinolin-1-yl)ethyl]-1-propanesulfonamide | U.S. Pat. No. 6,331,539 Example 17 |
| IRM13 | N-{2-[2-(4-amino-2-ethyl-1H-imidazo[4,5-c]quinolin-1-yl)ethoxy]ethyl}-N'-phenylurea | U.S. Ser. No. 10/164816 Example 50 |
| IRM14 | 1-{4-[(3,5-dichlorophenyl)thio]butyl}-2-ethyl-1H-imidazo[4,5-c]quinolin-4-amine | U.S. Ser. No. 10/165222 Example 44 |
| IRM15 | N-{2-[4-amino-2-(ethoxymethyl)-1H-imidazo[4,5-c]quinolin-1-yl]ethyl}-N'-(3-cyanophenyl)urea | WO 00/76518# |
| IRM16 | 4-amino-2-ethoxymethyl-α,α-dimethyl-6,7,8,9-tetrahydro-1H-imidazo[4,5-c]quinoline-1-ethanol | U.S. Pat. No. 5,352,784 Example 91 |
| IRM17 | 4-amino-α,α-dimethyl-2-methoxyethyl-1H-imidazo[4,5-c]quinoline-1-ethanol | U.S. Pat. No. 5,389,640 Example 111 |
| IRM18 | 4-amino-2-butyl-α,α,6,7-tetramethyl-1H-imidazo[4,5-c]pyridine-1-ethanol | U.S. Pat. No. 5,494,916 Example 52 |
| IRM19 | N-(2-{2-[4-amino-2-(2-methoxyethyl)-1H-imidazo[4,5-c]quinolin-1-yl]ethoxy}ethyl)-N'-phenylurea | WO 02/46191 Example 1 |
| IRM20 | 1-{4-[(3,5-dichlorophenyl)sulfonyl]butyl}-2-ethyl-1H-imidazo[4,5-c]quinolin-4-amine | U.S. Ser. No. 10/165222 Example 46 |
| IRM21 | N-{2-[4-amino-2-(2-methoxyethyl)-1H-imidazo[4,5-c]quinolin-1-yl]ethyl}-N'-sec-butylthiourea | WO 00/76518# |
| IRM22 | N-{2-[4-amino-2-(2-methoxyethyl)-6,7,8,9-tetrahydro-1H-imidazo[4,5-c]quinolin-1-yl]-1,1-dimethylethyl}methanesulfonamide | U.S. Pat. No. 6,331,539# |
| IRM23 | $N^2$-[2-(4-amino-2-butyl-1H-imidazo[4,5-c][1,5]naphthyridin-1-yl)ethyl]-5-bromo-2-furamide | U.S. Pat. No. 6,194,425 Example 206 |
| IRM24 | $N^1$-[4-(4-amino-1H-imidazo[4,5-c]quinolin-1-yl)butyl]-1-naphthamide | U.S. Pat. No. 6,451,810 Example 38 |
| IRM25 | 1-(2-{3-[3-(dimethylamino)phenyl]propoxy}ethyl)-1H-imidazo[4,5-c]quinolin-4-amine | WO 02/46189 Example 15 |
| IRM26 | N-{2-[4-amino-2-(ethoxymethyl)-6,7-dimethyl-1H-imidazo[4,5-c]pyridin-1-yl]ethyl}methanesulfonamide | U.S. Pat. No. 6,525,064# |
| IRM27 | 2-butylthiazolo[4,5-c]quinolin-4-amine | U.S. Pat. No. 6,110,929 Example 18 |
| IRM28 | $N^3$-[4-(4-amino-1H-imidazo[4,5-c]quinolin-1-yl)butyl]-3-quinolinecarboxamide | U.S. Pat. No. 6,451,810 Example 40 |
| IRM29 | 1-{[2-(4-nitrophenoxy)ethoxy]methyl}-1H-imidazo[4,5-c]quinolin-4-amine | WO 02/46189 Example 83 |
| IRM30 | $N^2$-[4-(4-amino-2-butyl-1H-imidazo[4,5-c]quinolin-1-yl)butyl]-2-naphthalenesulfonamide | U.S. Pat. No. 6,331,539 Example 32 |
| IRM31 | 1-[2-(benzo[b]furan-2-ylmethoxy)ethyl]-1H-imidazo[4,5-c]quinolin-4-amine | WO 02/46193 Example 12 |
| IRM32 | N-[3-(4-amino-2-butyl-1H-imidazo[4,5-c]quinolin-1-yl)propyl]-N'-phenylurea | U.S. Ser. No. 10/028255 Example 146 |
| IRM33 | 1-(5-benzenesulfonyl-pentyl)-2,6,7-trimethyl-1H-imidazo[4,5-c]pyridin-4-ylamine | U.S. Ser. No. 60/387,268# |
| IRM34 | 4-amino-α,α,2-trimethyl-1H-imidazo[4,5-c]quinoline-1-ethanol | U.S. Pat. No. 5,266,575 Example C1 |
| IRM35 | 1-{2-[3-(3-pyridyl)propoxy]ethyl}-1H-imidazo[4,5-c]quinolin-4-amine | WO 02/46193 Example 33 |

TABLE 4-continued

| Compound | Chemical Name | Reference |
|---|---|---|
| IRM36 | N-[4-(4-amino-2-ethyl-1H-imidazo[4,5-c]quinolin-1-yl)butyl]methanesulfonamide | U.S. Pat. No. 6,331,539[#] |
| IRM37 | N-{3-[4-amino-2-(ethoxymethyl)-1H-imidazo[4,5-c]quinolin-1-yl]propyl}-N'-(3-cyanophenyl)thiourea | WO 00/76518[#] |
| IRM38 | N-[4-(4-amino-2-methyl-1H-imidazo[4,5-c]quinolin-1-yl)butyl]piperidine-1-carboxamide | U.S. Pat. No. 6,541,485[#] |
| IRM39 | N-[2-(4-amino-2-ethyl-1H-imidazo[4,5-c]quinolin-1-yl)-1,1-dimethylethyl]-N'-phenylurea | U.S. Pat. No. 6,573,273[#] |
| IRM40 | 4-amino-α,α-dimethyl-2-ethoxymethyl-1H-imidazo[4,5-c]quinolin-1-ethanol | U.S. Pat. No. 5,389,640 Example 99 |
| IRM41 | 1-(2-methylpropyl)-1H-imidazo[4,5-c]quinolin-4-amine | U.S. Pat. No. 4,689,338 Example 99 |
| IRM42 | $N^2$-[2-(4-amino-2-butyl-1H-imidazo[4,5-c][1,5]naphthyridin-1-yl)ethyl]-5-bromo-2-thiophenecarboxamide | U.S. Pat. No. 6,194,425 Example 204 |
| IRM43 | N-[8-(4-amino-1H-imidazo[4,5-c]quinolin-1-yl)octyl]benzamide | U.S. Pat. No. 2003/0144283 Example 191 |
| IRM44 | 2-[(4-amino-2-butyl-1-methyl-1H-imidazo[4,5-c]quinolin-8-yl)oxy]-1-morpholin-1-ylethanone | U.S. Ser. No. 60/508,634 Example 32 |
| IRM45 | 1-{1-[(3-phenylpropoxy)methyl]propyl}-1H-imidazo[4,5-c]quinolin-4-amine | U.S. Pat. No. 6,670,372 Example 109 |
| IRM46 | 4-(4-amino-1H-imidazo[4,5-c]quinolin-1-yl)-1-phenylbutan-1-one | U.S. Ser. No. 60/524,961 Example 3 |
| IRM47 | 2-methyl-1-{2-[(3-phenylprop-2-ynyl)oxy]ethyl}-1H-imidazo[4,5-c]quinolin-4-amine | U.S. Pat. No. 6,670,372 Example 118 |
| IRM48 | N-{4-[4-amino-8-(benzyloxy)-2-ethyl-1H-imidazo[4,5-c]quinolin-1-yl]butyl}benzamide | U.S. Ser. No. 60/498,270 Example 82 |
| IRM49 | N-(2-{2-[4-amino-2-(2-methoxyethyl)-1H-imidazo[4,5-c]quinolin-1-yl]ethoxy}ethyl)morpholine-4-carboxamide | U.S. Pat. No. 6,656,938 Example 5 |
| IRM50 | 2-ethyl-1-[4-(isopropylthio)butyl-1H-imidazo[4,5-c]quinolin-4-amine | U.S. Pat. No. 6,667,312 Example 43 |
| IRM51 | N,N'-bis(2-{2-[4-amino-2-(2-methoxyethyl)-1H-imidazo[4,5-c]quinolin-1-yl]ethoxy}ethyl)terephthalamide | U.S. Ser. No. 10/670,957 Example 6 |

[#]This compound is not specifically exemplified but can be readily prepared using the synthetic methods disclosed in the cited reference.

Cells

HEK293 cells—immortalized human embryonic kidney cells, available from American Type Culture Collection, Manassas, Va., ATCC No. CRL-1573.

Namalwa cells—Burkitt's Lymphoma lymphoblastoid cells, available from ATCC American Type Culture Collection, Manassas, Va., ATCC No. CRL-1432.

Example 1

HEK293 medium was prepared from 90% Minimum Essential Medium (MEM) with 2 mM L-glutamine and Earle's Balanced Salt Solution (Invitrogen Corp., Rockville, Md.) adjusted to contain 1.5 g/L sodium bicarbonate, 0.1 mM non-essential amino acids, and 1.0 mM sodium pyruvate; 10% heat-inactivated fetal calf serum. HEK293 cells were cultured by incubating cells in HEK293 medium overnight at 37° C., 8% $CO_2$.

Twenty-four hours before transfection, HEK293 cells were adhered to a 10 cm dish (Corning 430167, Corning Inc., Corning, N.Y.) at 37° C., 8% $CO_2$. The cells were co-transfected with (1) pIRES (BD Biosciences Clontech, Palo Alto, Calif.) either (a) unmodified (HEK293-vector), (b) containing an expressible human TLR7 gene (HEK293-TLR7), or (c) containing an expressible human TLR8 gene (HEK293-TLR8), and (2) NFkB-luc reporter (Stratagene, La Jolla, Calif.) in a 10:1 ratio with Fugene 6 transfection reagent (Roche Diagnostics Corp., Indianapolis, Ind.) following the manufacturer's instructions. The plates were incubated for 24 hours following transfection and then selected in G-418 (400 μg/mL) for two weeks. The G-418-resistant cells containing either the expressible TLR7 gene, the expressible TLR8 gene, or the empty vector were expanded in HEK293 medium supplemented with G-418 for stimulation experiments.

The transfected cells were plated in white opaque 96 well plates (Costar 3917, Corning Inc., Corning, N.Y.) at a concentration of 5×1 cells per well in 100 μL of HEK293 media and incubated at 37° C., 8% $CO_2$ for 4 hours. The cells were stimulated with 1 μL of IRM compounds at 1 mM in DMSO (final IRM concentration of 10 μM) or 1 μL DMSO as a control. The plates were then incubated an additional 16 hours at 37° C., 5% $CO_2$. The luciferase signal was read using the LucLite kit (Packard Instrument Co., Meriden, Conn.). Luminescence was measured on an LMAX luminometer (Molecular Devices Corp., Sunnyvale, Calif.).

Results are shown in Table 5 and are expressed as fold increase of NFκB-induced luciferase signal compared to a DMSO control.

TABLE 5

| Compound | TLR7 | TLR8 |
|---|---|---|
| IRM1 | 4.05 | 1.02 |
| IRM2 | 4.16 | 0.91 |
| IRM3 | 6.37 | 1.14 |
| IRM4 | 4.98 | 1.06 |
| IRM5 | 3.38 | 0.94 |
| IRM6 | 8.46 | 0.90 |
| IRM7 | 6.22 | 0.86 |
| IRM8 | 6.04 | 0.99 |
| IRM9 | 1.53 | 10.11 |
| IRM10 | 0.64 | 9.24 |
| IRM11 | 1.44 | 10.69 |
| IRM12 | 1.16 | 8.84 |
| IRM13 | 0.86 | 6.25 |
| IRM14 | 0.67 | 4.18 |
| IRM15 | 0.92 | 5.52 |
| IRM16 | 5.54 | 8.64 |
| IRM17 | 2.53 | 10.18 |
| IRM18 | 5.06 | 2.77 |
| IRM19 | 2.45 | 7.25 |
| IRM20 | 4.22 | 6.04 |
| IRM21 | 7.08 | 5.92 |
| IRM22 | 6.57 | 7.37 |

Example 2

Unless otherwise indicated, all incubations were performed at 37° C. with 5% $CO_2$ at 98% humidity.

Culture medium was prepared from complete RPMI 1640 medium (BioSource International, Inc., Camarillo, Calif.). Fetal bovine serum (Atlas Biologicals, Inc., Ft. Collins, Colo.) was added to a final concentration of 7.5% (vol/vol); L-glutamine (BioSource International, Inc.) was added to 5 mM; and sodium pyruvate (BioSource International, Inc.) was added to 1 mM.

Namalwa cells were grown by incubation in culture medium overnight. Cells were harvested by centrifugation in a tabletop centrifuge (1200 RPM for 5 minutes), and then resuspended in phosphate buffered sucrose to a concentration of $1.3 \times 10^7$ cells/mL.

For each transfection, a 750 µL aliquot of the cell suspension was placed in an electroporation cuvette with 4 mm gaps. 10 µg of the pIFN-α1-luc vector and 10 µg of the pCI-TLR6 vector were added to the electroporation cuvette. The cell and vector mixtures were incubated at room temperature for 5 minutes. The cells were electroporated using a BioRad Gene Pulser (BioRad Laboratories, Hercules, Calif.) set to at 500 µF capacitance and 0.27 volts, then incubated at room temperature for 5 minutes.

The electroporated cells were suspended in 10 mLs of culture medium and incubated overnight. Dead cells and debris were removed after 24 hours using a MACS Dead Cell Removal kit (Miltenyi Biotec, Auburn, Calif.). Cells were resuspended in 10 mL of culture medium and incubated for an additional 24 hours.

Transfected cells were selected by adding G418 (Promega Corp., Madison, Wis.) to a final concentration of 1 mg/mL and incubating the cells for seven days.

The selected transfected cells were counted and resuspended to a concentration of $1 \times 10^6$ cell per mL in culture medium. 100 µl aliquots of cells were placed in the wells of a white-walled, white-bottomed 96-well plate (Corning, Inc., Corning, N.Y.). 1.0 µL of an IRM compound from Table 1 (prepared at 1 mM in 100% DMSO) was added to some cell aliquots so that the final concentration of IRM compound was 10 µM. As a positive control, some cell aliquots were incubated with Sendai virus instead of IRM compound. As a negative control, some cell aliquots were incubated with DMSO without IRM compound. In all cases, the cells were incubated for 18 hours.

The plates were equilibrated to room temperature before one volume of reconstituted LucLight Plus (Packard Instruments, Meriden, Conn.) was added to each aliquot of cells. Each well of the plate was read on an LJL Analyst (LJL Biosystems, Inc., Sunnyvale, Calif.) set with a 5 minute dark adapt. Results are shown in Table 6 and are expressed as fold increase of the IFN-α1-induced luciferase signal compared to a DMSO control.

TABLE 6

| Compound | TLR6 | TLR7 |
|---|---|---|
| IRM23 | 0.90 | 2.02 |
| IRM24 | 0.00 | 3.38 |
| IRM25 | 0.04 | 2.89 |
| IRM26 | 1.50 | 2.48 |
| IRM42 | 0.98 | 3.54 |
| IRM43 | 1.07 | 2.17 |
| IRM14 | 2.73 | 1.40 |
| IRM27 | 6.28 | 1.32 |
| IRM28 | 2.27 | 0.96 |
| IRM29 | 4.57 | 1.32 |
| IRM30 | 4.38 | 1.28 |
| IRM31 | 3.40 | 1.63 |
| IRM32 | 7.47 | 1.77 |
| IRM33 | 13.12 | 1.99 |
| IRM44 | 6.10 | 1.60 |
| IRM45 | 5.56 | 1.87 |
| IRM46 | 3.75 | 1.83 |
| IRM47 | 9.42 | 1.91 |
| IRM48 | 4.56 | 1.62 |
| IRM49 | 10.92 | 1.95 |
| IRM50 | 8.80 | 1.91 |
| IRM51 | 3.67 | 1.74 |
| IRM1 | 7.93 | 2.43 |
| IRM3 | 10.24 | 2.86 |
| IRM6 | 13.61 | 3.09 |
| IRM8 | 12.49 | 2.89 |
| IRM16 | 12.95 | 2.96 |
| IRM21 | 17.98 | 3.48 |
| IRM22 | 16.25 | 3.59 |
| IRM34 | 10.80 | 3.37 |
| IRM35 | 6.72 | 2.33 |
| IRM19 | 12.60 | 2.63 |

Example 3

Selective Modulation of pDCs and mDCs by TLR-Selective Compounds

Whole blood was collected in 60 mL syringes filled with 750 µL of 0.5 M EDTA, pH 8.0 (Invitrogen Corp., Grand Island, N.Y.). Blood was diluted 1:1 in Dulbecco's Phosphate Buffered Saline without calcium or magnesium (DPBS, Biosource International, Camarillo, Calif.) and overlayed with Histopaque-1077 (Sigma Chemical Co., St. Louis, Mo.). Cells were centrifuged at 2000 RPM for 30 minutes at 25° C. The buffy coat layer was isolated and washed three times with DPBS at 1350 RPM for 10 minutes at 25° C.

The plasmacytoid dendritic cells (pDC) were isolated from the PBMCs using the Miltenyi Microbead technology system (Miltenyi BioTec, Auburn, Calif.). PBMCs were resuspended in 4° C. separation buffer (PBS- pH 7.2, 0.5% BSA-2.5 gm, 2 mM 0.5M EDTA) at 30 µl per $10^7$ total cells. BDCA-4 microbeads (cat. no. 130-090-532, Miltenyi BioTec) and FcR Blocking Reagent (cat. no. 130-059-901, Miltenyi BioTec) were added at 10 µL per $10^7$ total cells and incubated for 15 minutes at 4° C. The cells were washed by adding 1 mL separation buffer per $10^7$ cells and centrifuging at 1350 RPM for 10 minutes at 25° C. The cells were resuspended in 500 µL of separation buffer per $10^8$ total cells. BDCA-4$^+$pDCs were enriched by Miltenyi AUTOMACS using POSSELD software. The cells retained in the column were eluted into a sterile 50 mL polystyrene conical tube. The BDCA-4$^+$pDCcs were centrifuged at 1350 RPM for 10 minutes at 25° C. and resuspended in X-VIVO 20 (Cambrex Bio Science Walkersville, Inc., Walkersville, Md.) supplemented with 10 ng/ml IL-3 (PeproTech, Inc., Rocky Hill, N.J.) at $1\times10^6$ cells/mL.

The blood myeloid dendritic cells (mDC) were isolated from the BDCA-4 negative cell fraction using the Miltenyi Microbead technology system (Miltenyi BioTec, Auburn, Calif.). Cells were resuspended in 4° C. separation buffer (PBS- pH 7.2, 0.5% BSA-2.5 gm, 2 mM 0.5M EDTA) at 20 µl per $10^7$ total cells. BDCA-1-biotin antibody, CD19 microbeads (cat. no. 130-090-506, Miltenyi BioTec) and FcR Blocking Reagent (cat. no. 130-059-901, Miltenyi BioTec) were each added at 10 µL per $10^7$ total cells and incubated for 15 minutes at 4° C. The cells were washed by increasing the volume by 1 ml separation buffer per $10^7$ cells and centrifuged at 1350 RPM for 10 minutes at 25° C. The cells were resuspended in 500 µL of separation buffer per $10^8$ total cells. CD19 microbead labeled cells were removed on the Miltenyi Automacs (cat. no. 201-01, Miltenyi BioTec) using DEPLETES software. Cells from the CD19 negative fraction were centrifuged at 1350 RPM for 10 minutes at 25° C. and resuspended in 400 µL of separation buffer per $10^8$ total cells. Anti-Biotin microbeads were added at 110 µL per 107 total cells and incubated for 15 minutes at 4° C. The cells were centrifuged at 1350 RPM for 10 minutes at 25° C. and resuspended in 500 µL of separation buffer per $10^8$ total cells. BDCA-1$^+$mDCs were enriched using the Miltenyi Automacs POSSELD software. The cells retained in the column were eluted into a sterile 50 mL polystyrene conical tube. The BDCA-1$^+$cells were centrifuged at 1350 RPM for 10 minutes at 25° C. and resuspended in X-VIVO 20 (Cambrex Bio Science Walkersville, Inc., Walkersville, Md.) at $1\times10^6$ cells/mL.

Blood dendritic cell subsets isolated as described were cultured overnight in the with 0.03% DMSO vehicle control, 1 µM IRM9, 1 µM IRM16, 1 µM IRM36, 3 µM CpG2216 (InvivoGen, Dan Diego, Calif.), or 20 ng/mL E. coli LPS (Sigma Chemical Co., St. Louis, Mo.). Compounds, reconstituted in dimethyl sulfoxide (DMSO, sterile cell culture grade, Sigma Chemical Co., St. Louis, Mo.) were added at 2× their final concentration to a 96-well flat-bottom sterile tissue culture polystyrene plate (Benton Dickinson Labware, Franklin Lakes, N.J.). Cells were then added at 2× the final concentration (final cell concentration is $1\times10^6$ cells/mL). Plates were incubated for 16-24 hours at 37° C., 5% $CO_2$. After incubation, plates were centrifuged at 1000 RPM for 10 minutes at 25° C. Supernatants were transferred to a 0.75 mL sterile polypropylene Matrix box (Matrix, Hudson, N.Y.) and stored at –20° C. for future cytokine analysis.

Cells were stained with antibodies specific for CD80 and HLA-DR and analyzed by flow cytometry. The results are shown in FIGS. 1 and 2. The cells that stain positively for HLA-DR with increased staining for CD80 identify dendritic cells that were activated as a result of the TLR agonist stimulation.

Example 4

Myeloid DCs were isolated and incubated with vehicle or IRM compound (IRM9, IRM36, IRM37, IRM38, IRM39, IRM40, or IRM41) as described in Example 3, except that the final concentration of IRM compound was 3.0 µM.

IL-12 analysis was performed using IGEN analysis. More than two hours prior to performing the analysis, a 1:20 dilution of M-280 Streptavidin Dynabeads was prepared in IGEN buffer. Also, a 1 µg/mL solution of biotinylated IL-12 antibody (Cat. No. AHC7129, Biosource International, Camarillo, Calif.) in IGEN buffer was prepared. The 1:20 Dynabeads solution and the biotinylated antibody solution were mixed together and incubated 30 minutes at room temperature, then stored at 4° C. until the analysis was performed.

To perform the analysis, 50 µL of the Dynabeads/biotinylated antibody solution was added to each well of a 96-well plate. Next, 25 µL of 1 µg/mL solution of Ori-tagged IL-12 antibody (Cat. No. 8122, Biosource International, Camarillo, Calif.) in IGEN buffer was added to each well. 25 µL of sample was added to each well, each sample containing either a standard dilution or an experimental sample.

The 96-well plate was tapped to mix the contents of each well, covered with plate sealer, and incubated at room temperature for 2.5 hours. Following the incubation, 100 µL of IGEN PBS Buffer was added to each well for a total assay volume of 200 µL and read on the IGEN M-8 Analyzer (IGEN International, Inc., Gaithersburg, Md.) using the hIL-12 protocol. Results are expressed as pg/mL of IL-12 and are shown in Table 7.

TABLE 7

|  | vehicle | IRM40 | IRM36 | IRM38 | IRM41 | IRM9 | IRM37 | IRM39 |
| --- | --- | --- | --- | --- | --- | --- | --- | --- |
| donor3 | 0 | 517 | 57 | 17 | 17 | 693 | 296 | 280 |
| donor4 | 0 | 765 | 77 | 20 | 39 | 1041 | 491 | 400 |

The complete disclosures of the patents, patent documents and publications cited herein are incorporated by reference in their entirety as if each were individually incorporated. In case of conflict, the present specification, including definitions, shall control.

Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A method of identifying a compound that selectively modulates at least one TLR7-mediated cellular activity or at least one TLR8-mediated cellular activity, the method comprising:

contacting a test compound with human cells that naturally express TLR7 and detecting modulation of a TLR7-mediated cellular activity;

contacting the test compound with human cells that naturally express TLR8 and detecting modulation of a TLR8-mediated cellular activity; and identifying the test compound as a compound that selectively modulates at least one TLR7-mediated cellular activity if the test compound modulates the TLR7-mediated cellular activity to a greater extent than it modulates the TLR8-mediated cellular activity and identifying the test compound as a compound that selectively modulates at least one TLR8-mediated cellular activity if the test compound modulates the TLR8-mediated cellular activity to a greater extent than it modulates the TLR7-mediated cellular activity, wherein the TLR7 mediated cellular activity or TLR8 mediated cellular activity comprises inducing production of a cytokine, co-stimulatory marker, intercellular adhesion molecule, proliferation/maturation marker, or a combination thereof.

2. The method of claim 1 wherein the compound modulates a TLR7-mediated cellular activity and does not modulate a TLR8-mediated cellular activity.

3. The method of claim 1 wherein the compound modulates a TLR8-mediated cellular activity and does not modulate a TLR7-mediated cellular activity.

4. The method of claim 1 wherein the TLR7-mediated cellular activity or TLR8-mediated cellular activity is inducing production of a cytokine selected from the group consisting of: TNF-α, a Type I interferon, IFN-γ, IL-1, IL-6, IL-8, IL-10, IL-12, MIP-1, MCP-1, and combinations thereof.

5. The method of claim 1 wherein the TLR7-mediated cellular activity or TLR8-mediated cellular activity is inducing production of a co-stimulatory marker.

6. The method of claim 1 wherein the TLR7-mediated cellular activity or TLR8-mediated cellular activity is inducing production of an intercellular adhesion molecule.

7. The method of claim 1 wherein the TLR7-mediated cellular activity or TLR8-mediated cellular activity is inducing production of a proliferation/maturation marker.

8. The method of claim 1 wherein human cells that naturally express TLR7 comprise plasmacytoid dendritic cells and human cells that naturally express TLR8 comprise myeloid dendritic cells.

9. The method of claim 1, wherein the greater extent comprises at least a two fold increase.

* * * * *

UNITED STATES PATENT AND TRADEMARK OFFICE
CERTIFICATE OF CORRECTION

PATENT NO. : 7,485,432 B2  
APPLICATION NO. : 10/788731  
DATED : February 3, 2009  
INVENTOR(S) : Fink et al.

Page 1 of 1

It is certified that error appears in the above-identified patent and that said Letters Patent is hereby corrected as shown below:

Column 20
Line 51, delete "picomavirus" and insert -- picornavirus --, therefor.

Column 21
Line 8, delete "camii" and insert -- carnii --, therefor.

Column 28
Line 56, delete "5x1" and insert -- $5 \times 10^4$ --, therefor.

Column 30
Lines 10-12, delete "Results are shown in Table 6 and are expressed as fold increase of the IFN-α1-induced luciferase signal compared to a DMSO control." and insert the same on Col. 30, Line 11, as a new paragraph.

Line 64, delete "107" and insert -- $10^7$ --, therefor.

Column 31
Line 30, delete "110 μL per 107" and insert -- 10 μL per $10^7$ --, therefor.

Signed and Sealed this

Twenty-second Day of December, 2009

David J. Kappos  
*Director of the United States Patent and Trademark Office*